United States Patent
Esaki et al.

(10) Patent No.: US 10,463,677 B2
(45) Date of Patent: Nov. 5, 2019

(54) COMPOSITION CONTAINING SULFOALKYL ETHER CYCLODEXTRIN AND LATANOPROST

(75) Inventors: Naomi Esaki, Lenexa, KS (US); James D. Pipkin, Lawrence, KS (US)

(73) Assignee: CyDex Pharmaceuticals, Inc., San Diego, CA (US)

( * ) Notice: Subject to any disclaimer, the term of this patent is extended or adjusted under 35 U.S.C. 154(b) by 407 days.

(21) Appl. No.: 13/128,319

(22) PCT Filed: Nov. 7, 2008

(86) PCT No.: PCT/US2008/082730
§ 371 (c)(1),
(2), (4) Date: Sep. 26, 2011

(87) PCT Pub. No.: WO2010/053487
PCT Pub. Date: May 14, 2010

(65) Prior Publication Data
US 2012/0021013 A1  Jan. 26, 2012

(51) Int. Cl.
A61K 9/00 (2006.01)
A61K 31/5575 (2006.01)
A61P 27/02 (2006.01)
A61K 31/557 (2006.01)
A61K 31/74 (2006.01)
A61K 47/40 (2006.01)

(52) U.S. Cl.
CPC .......... *A61K 31/557* (2013.01); *A61K 9/0048* (2013.01); *A61K 31/74* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 3,426,011 A | 2/1969 | Parmerter et al. | |
| 5,134,127 A | 7/1992 | Stella et al. | |
| 5,241,059 A | 8/1993 | Yoshinaga | |
| 5,324,718 A | 6/1994 | Loftsson | |
| 5,362,860 A | 11/1994 | Huang et al. | |
| 5,376,645 A | 12/1994 | Stella et al. | |
| 5,472,954 A | 12/1995 | Loftsson | |
| 5,512,665 A | 4/1996 | Uchiyama et al. | |
| 5,578,719 A | 11/1996 | Gadelle et al. | |
| 5,760,015 A | 6/1998 | Joullié et al. | |
| 5,846,954 A | 12/1998 | Joullié et al. | |
| 5,874,418 A | 2/1999 | Stella et al. | |
| 6,046,177 A | 4/2000 | Stella et al. | |
| 6,133,248 A | 10/2000 | Stella | |
| 6,153,746 A | 11/2000 | Shah et al. | |
| 6,204,256 B1 | 3/2001 | Shalaby et al. | |
| 6,210,974 B1 | 4/2001 | Gold | |
| 6,383,471 B1 | 5/2002 | Chen et al. | |
| 6,451,339 B2 | 9/2002 | Patel et al. | |
| 6,479,467 B1 | 11/2002 | Buchanan et al. | |
| 6,524,595 B1 | 2/2003 | Perrier et al. | |
| 6,569,463 B2 | 5/2003 | Patel et al. | |
| 6,610,671 B2 | 8/2003 | Buchanan et al. | |
| 6,923,988 B2 | 8/2005 | Patel et al. | |
| 7,629,331 B2 | 12/2009 | Pipkin et al. | |
| 7,635,773 B2 | 12/2009 | Antle | |
| 8,236,782 B2 | 8/2012 | Mosher et al. | |
| 8,343,995 B2 | 1/2013 | Mosher et al. | |
| 2003/0104048 A1 | 6/2003 | Patel et al. | |
| 2004/0072809 A1 | 4/2004 | Demopulos et al. | |
| 2004/0109888 A1 | 6/2004 | Pun et al. | |
| 2004/0115234 A1* | 6/2004 | Gewirtz | 424/401 |
| 2005/0096296 A1 | 5/2005 | Fikstad et al. | |
| 2005/0164986 A1 | 7/2005 | Mosher et al. | |
| 2005/0186267 A1 | 8/2005 | Thompson et al. | |
| 2005/0228048 A1* | 10/2005 | Asada et al. | 514/561 |
| 2005/0256083 A1* | 11/2005 | Chang et al. | 514/58 |
| 2005/0276841 A1 | 12/2005 | Davis et al. | |
| 2006/0003002 A1 | 1/2006 | Fikstad et al. | |
| 2006/0172972 A1* | 8/2006 | Bhushan et al. | 514/79 |
| 2007/0020196 A1 | 1/2007 | Pipkin et al. | |
| 2008/0021101 A1* | 1/2008 | Jimenez-Bayardo | A61K 31/5575 514/530 |
| 2009/0012042 A1 | 1/2009 | Ren et al. | |
| 2009/0123540 A1 | 5/2009 | Pipkin et al. | |
| 2009/0270348 A1 | 10/2009 | Antle | |
| 2011/0028477 A1* | 2/2011 | Aleo | A61K 9/0048 514/236.2 |

FOREIGN PATENT DOCUMENTS

| | | |
|---|---|---|
| EP | 0 579 435 | 1/1994 |
| EP | 001478404 | * 11/2004 |
| JP | 05-001102 | 1/1993 |
| WO | WO 91/11172 | 8/1991 |
| WO | WO 94/02518 | 2/1994 |
| WO | WO 96/06581 A1 | 3/1996 |
| WO | WO 99/42111 | 8/1999 |
| WO | WO 01/40316 A1 | 6/2001 |
| WO | WO 2002/056915 A2 | 7/2002 |
| WO | WO 03/002152 | 1/2003 |
| WO | WO 05/065649 | 7/2005 |
| WO | WO 05/117911 | 12/2005 |
| WO | WO 2008/029282 | 3/2008 |
| WO | WO 08/134600 | 11/2008 |
| WO | WO 08/134601 | 11/2008 |
| WO | WO 2008/134600 A1 | 11/2008 |
| WO | WO 09/018069 | 2/2009 |
| WO | WO 2010/045281 A2 | 4/2010 |

OTHER PUBLICATIONS

Ueda H, Ou D, Endo T, Nagase H, Tomono K, Nagai T. "Evaluation of a sulfobutyl ether beta-cyclodextrin as a solubilizing/stabilizing agent for several drugs". Drug Dev Ind Pharm. Sep. 1998;24(9): 863-7.*

(Continued)

*Primary Examiner* — Nicole P Babson
(74) *Attorney, Agent, or Firm* — Knobbe, Martens, Olson & Bear LLP

(57) ABSTRACT

An aqueous composition of latanoprost and SAE-CD is provided. The composition possesses improved stability over otherwise similar compositions excluding SAE-CD. Methods of and systems for treating diseases, disorders, conditions or symptoms of the eye that are therapeutically responsive to latanoprost are also provided.

19 Claims, 3 Drawing Sheets

(56) References Cited

OTHER PUBLICATIONS

ChemSpider. CSID:4445566, http://www.chemspider.com/Chemical-Structure.4445566.html. accessed 19:28, Oct. 23, 2013.*

Stella VJ, He Q. "Cyclodextrins" Toxicol Pathol. Jan. 2008;36(1):30-42.*

National Center for Biotechnology Information. PubChem Compound Database; CID=44134771, https://pubchem.ncbi.nlm.nih.gov/compound/44134771 (accessed Jan. 5, 2016).*

Adam, J.M., et al., "Cyclodextrin-Derived Host Molecules as Reversal Agents for the Neuromuscular Blocker Rocuronium Bromide: Synthesis and Structure-Activity Relationships," *J. Med. Chem.* 45:1806-1816, American Chemical Society, United States (2002).

Lammers, J.N.J.J., and Van Diemen, A.J.G., "Properties of Cyclodextrins, Part VIII: Determination of the composition of inclusion complexes of hexane and 2,3-dimethylbutane with cyclodextrin derivatives in aqueous solution," *Rec. Trav. Chim.* 91:733-742, Société Chimique Neerlandaise, Netherlands (1972).

Lammers, J.N.J.J., et al., "Properties of Cyclodextrins: PartVI. Water-Soluble Cyclodextrin-Derivatives. Preparation and Analysis," *Die Stärke* 5:167-171, Netherlands (1971).

Qu, Q., et al., "Sulfoalkyl Ether β-Cyclodextrin Derivatives: Synthesis and Characterizations," *Journal of Inclusion Phenomena and Macrocyclic Chemistry* 43:213-221, Kluwer Academic Publishers, Netherlands (2002).

Tarver, G.J., et al., "2-O-Substituted Cyclodextrins as Reversal Agents for the Neuromuscular Blocker Rocuronium Bromide," *Bioorganic Medicinal Chemistry* 10:1819-1827, Elsevier Science Ltd., England (2002).

International Search Report for International Application No. PCT/US08/82730, United States Patent Office, United States, dated Jan. 30, 2009.

Chiang et al., 1979, Acid-catalysed hydrolysis of prostacyclin: origin of the unused lability, J.C.S. Chem Comm, pp. 129-130.

Fridriksdottir et al., 1997, Formulation and testing of methazolamide cyclodextrin eye drop solutions, Journal of Controlled Release, 44(1):95-99.

Fridriksdottir et al., Jan. 1996, Design and in vivo testing of 17β-estradiol HPβCD sublingual tablets, Die Pharmazie, 51(1):39-42.

Fridriksdottir et al., Mar. 31-Apr. 2, 1996, Solubilization of β-cyclodextrin: the effect of polymers and various drugs on the solubility of β-cyclodextrin, Proceedings of the Eighth International Symposium on Cyclodextrins, eds. Szejtli et al., Budapest, 373-376.

Higuchi et al., 1965, Phase Solubility Techniques, in Advances in Analytical Chemistry and Instrumentation, vol. 4, pp. 117-212, Reilly, C., ed, John Wiley & Sons Inc., United Kingdom.

Kristinsson et al., 1996, Dexamethasone-cyclodextrin-polymer co-complexes in aqueous eye drops, Investigative Ophthalmology & Visual Science, 37(6):1199-1203.

Loftsson et al., 1994, The effect of polyvinylpyrrolidone and hydroxypropyl methylcellulose on HPβCD complexation of hydrocortisone and its permeability through hairless mouse skin, European Journal of Pharmaceutical Sciences, 2:297-301.

Loftsson et al., 1994, The effect of water-soluble polymers on drug-cyclodextrin complexation, International Journal of Pharmaceutics (Netherlands), 110(2):169-177.

Loftsson et al., 1996, Effects of cyclodextrins and polymers on topical drug delivery to the eye-evaluations in humans, Proceedings of the 23rd International Symposium on Controlled Release of Bioactive Materials, pp. 453-454.

Loftsson et al., 1997, Cyclodextrins as pharmaceutical excipients, Pharm. Technol. Eur. 9(5):26-34.

Loftsson et al., 1997, Enhanced complexation efficiency of cyclodextrins, Pharmaceutical Research, 14(11):S203.

Loftsson et al., 1998, Cyclodextrin solubilization of ETH-615, a zwitterionic drug, Drug Development and Industrial Pharmacy, 24(4):365-370.

Loftsson et al., 1998, The effect of water-soluble polymers on the aqueous solubility and complexing abilities of β-cyclodextrin, International Journal of Pharmaceutics, 163(1-2):115-121.

Loftsson et al., 1999, Methods to enhance the complexation efficiency of cyclodextrins, S.T.P. Pharma Sciences, 9(3):237-242.

Loftsson et al., 2001, Cyclodextrin solubilization of benzodiazepines: formulation of midazolam nasal spray, International Journal of Pharmaceutics, 212(1):29-40.

Loftsson et al., Apr. 11, 1994, The effect of hydroxypropyl methylcellulose on the release of dexamethasone from aqueous 2-hyroxypropyl-β-cyclodextrin formulations, International Journal of Pharmaceutics (Netherlands), 104:181-184.

Loftsson et al., Oct. 1994, Polymer-cyclodextrin-drug complexes, Pharmaceutical Research, 11(10):S225.

Loftsson et al., Oct. 1996, Pharmaceutical applications of cyclodextrins. 1. Drug solubilization and stabilization, Journal of Pharmaceutical Sciences, , 85(10):1017-1025.

Loftsson et al., Sep. 16, 1996, Drug-cyclodextrin-polymer ternary complexes, European Journal of Pharmaceutical Sciences, 4(SUPPL):S144.

Loftsson et al., Sep. 1996, Solubilization of β-cyclodextrin, Eur. J. Pharm. Sci, 4(Suppl.):S143.

Loftsson et al., Sep. 2001, Sustained drug delivery system based on a cationic polymer and an anionic drug/cyclodextrin complex, Pharmazie, 56(9):746-747.

Loftsson, 1996, Topically effective acetazolamide eye-drop solution in man, Pharmaceutical Sciences, 2(6):277-279.

Loftsson, 1998, Drug-cyclodextrin complexation in the presence of water soluble polymers: enhanced solubility and percutaneous transport, Abstracts of Papers Part 1, 216th ACS National Meeting, Boston, Aug. 23-27, CELL-016.

Loftsson, Apr. 2-6, 1995, The effect of polymers on cyclodextrin complexation, Book of Abstracts, 209th ACS National Meeting, 209(1):33-CELL.

Masson et al., 1999, Drug-cyclodextrin complexation in the presence of water-soluble polymers: enhanced solubility and percutaneous transport, ACS Symposium Series, 737 (Polysaccharide Applications), pp. 24-45.

Polymer Science, in Physical Pharmacy. Physical Chemical Principles in Pharmaceutical Sciences, 3rd edition, Martin et al., 1983, pp. 592-638.

Polymers and Macromolecules, in Physicochemical Principles of Pharmacy, 2nd edition, Florence et al., eds. pp. 281-334, 1988.

Remington's Pharmaceutical Sciences, 18th Edition, Gennaro ed., 1990, Hydrophilic Dispersons, pp. 291-294.

Savolainen et al., 1998, Co-administration of a water-soluble polymer increases the usefulness of cyclodextrins in solid oral dosage forms, Pharmaceutical Research, 15(11):1696-1701.

Savolainen et al., May 31-Jun. 3, 1998, Coadministration of a water-soluble polymer increases the usefulness of cyclodextrins in solid oral dosage forms, 9th Proceedings of the International Symposium on Cyclodextrins, Santiago de Comostela, Spain, eds. Labandeira et al., pp. 261-264.

Sigurdardottir et al., Dec. 29, 1995, The effect of polyvinylpyrrolidone on cyclodextrin complexation of hydrocortisone and its diffusion through hairless mouse skin, International Journal of Pharmaceutics (Netherlands), 126:73-78.

Uekama et al., Nov. 2001, Stabilizing and solubilizing effects of sulfobytul ether β-cyclodextrin on prostaglandin $E_1$ analogue, Pharmaceutical Research, 18(11):1578-1585.

Thorsteinn Loftsson, "Effects of cyclodextrins on the chemical stability of drugs in aqueous solutions" *Drug Stability*, 1, 22-33, (1995).

Arima H. et al., *Journal of Pharmaceutical Sciences* (2001) 90(6) 690-701.

Crini, Review: A History of Cyclodextrins, Chem. Rev. 2014; 114(21), pp. 10940-10975.

Cutrignelli A., et al., International Journal of Pharmaceutics, 332 (2007) 98-106.

Lamparczyk, et al., Retention Behavior of the Inclusion Complexes of Some Polycyclic Aromatic Hydrocarbons with β- Cyclodextrin, Chromatographia Feb. 1991; 31(3/4), pp. 157-162.

(56) References Cited

OTHER PUBLICATIONS

Loftsson, et al., Cyclodextrins in drug delivery, Expert Opin. Drug Deliv., 2005; 2(2), pp. 1-17.
Loftsson, *International Journal of Pharmaceutics*, 67 (1991) R5-R7.
Rasheed, et al., Cyclodextrins as Drug Carrier Molecule: A Review, Scientia Pharmaceutica 2008; 76(4), pp. 567-598.
Szejtli, J.: Cyclodextrins and Their Inclusion Complexes (Cyclodextrine and ihre Einschluβkomplexe). Verlag der Ungarischen Akademie der Wissenschaften. Akadémiai Kiadó, Budapest; 1982, p. 21, 75-86, and 97-101.
Szejtli, J., *Pharmaceutical Technology*, 1991, 15 (8), 24-38.
Teshima et al., Chemical & pharmaceutical bulletin (1989) 37(6), 1591-1594.
Uekama, et al., Cyclodextrin Drug Carrier Systems, Chem. Rev. 1998; 98(5), pp. 2045-2076.

\* cited by examiner

COMPOSITION CONTAINING SULFOALKYL ETHER CYCLODEXTRIN AND LATANOPROST

FIELD OF THE INVENTION

The present invention relates to compositions comprising sulfoalkyl ether cyclodextrin and latanoprost and to methods for their preparation and use.

BACKGROUND OF THE INVENTION

Latanoprost ((isopropyl (Z)-7-[(1R,2R,3R,5S)-3,5-dihydroxy-2-[(3R)-3-hydroxy-5-phenylpentyl]-cyclopentyl]hept-5-enoate) is an isopropyl ester analogue of prostaglandin F2α.

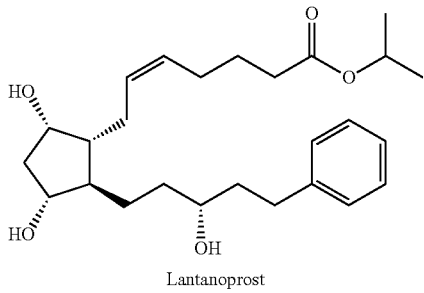 [SMILES: CC(C)OC(=O)CCC/C=C\C[C@@H]1[C@@H](CC[C@@H](O)CCc2ccccc2)[C@H](O)C[C@@H]1O]

Lantanoprost

The commercially available form of latanoprost (XALATAN®) includes no cyclodextrin and has issues concerning formulation stability. Latanoprost has been demonstrated to undergo substantial UV-B (320 nm to 290 nm) catalyzed photolytic degradation even under short exposure time, and it has been demonstrated to undergo substantial thermal and/or hydrolytic degradation at elevated temperatures in a pH dependent manner. The commercial formulation also contains BAK (benzalkonium chloride; 0.02%) as preservative; however, BAK has been reported to lead to corneal damage, and such activity is counterproductive to the therapeutic activity of latanoprost.

Sulfoalkyl ether cyclodextrin (SAE-CD) derivatives are polyanionic, hydrophilic, water soluble cyclodextrins derivatized with sulfoalkyl ether functional groups. SAE-CD derivatives are commercially available from CyDex Pharmaceuticals, Inc. (Lenexa, Kans.). SAE-CD is currently marketed under the trademarks CAPTISOL® and Advasep®.

CAPTISOL® has an average of about 7 sulfoalkyl ether substituents per cyclodextrin molecule. The anionic sulfobutyl ether substituent dramatically improves the aqueous solubility and safety of the parent cyclodextrin. Reversible, non-covalent, complexation of drugs with CAPTISOL® generally allows for increased solubility and, in some cases, increased stability of drugs in aqueous solutions.

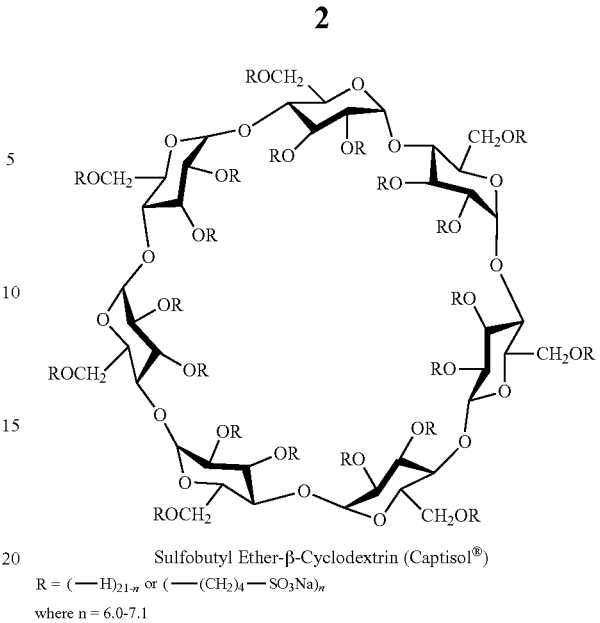

Sulfobutyl Ether-β-Cyclodextrin (Captisol®)
R = (—H)$_{21-n}$ or (—(CH$_2$)$_4$—SO$_3$Na)$_n$
where n = 6.0-7.1

SUMMARY OF THE INVENTION

The inventors have discovered that latanoprost in solution can be stabilized by SAE-CD under some conditions thereby reducing its photolytic and thermal or hydrolytic degradation upon storage in solution and thereby extending the shelf-life of aqueous compositions containing the same.

In some embodiments, the invention provides an aqueous composition comprising (or consisting essentially of): aqueous carrier; SAE-CD; and latanoprost, wherein the pH of the composition ranges from 5.5 to 7; the molar ratio of SAE-CD to latanoprost ranges from 2:1 to 40:1; the concentration of latanoprost ranges from 10 to 500 µg/mL; and the concentration of SAE-CD ranges from 1 to 100 mg/mL.

The invention also provides a method of treating a diseases, disorder, condition, or symptom that is therapeutically responsive to latanoprost, the method comprising: administering to a subject in need thereof a therapeutically effective amount of latanoprost in an aqueous composition according to the invention. In some embodiments, the composition is an ophthalmic composition that can be administered to the eye of a subject. In some embodiments, the administering is performed once or twice daily.

The invention also provides a system for treating, preventing or ameliorating a disease, disorder, condition or symptom of the eye in a subject in need thereof comprising: an aqueous composition comprising a therapeutically effective amount of latanoprost,
SAE-CD, and a pharmaceutically acceptable aqueous liquid carrier; and
an administration device for ophthalmic administration of the aqueous composition to the subject, wherein the composition is provided in the device.

The device for ophthalmic administration can be a dropper, pipette, drop-dispensing package, tube, eye spray device, or eye wash unit. The device can be adapted to emit 1-1000 µL of prostaglandin solution per unit dose. The device can comprise single or plural unit doses.

The device can include a reservoir comprising 0.1-100 mL of the aqueous composition, and the device can be adapted for single use or multiple use. Suitable dispensers are illustratively disclosed in International Patent Publication No. WO 96/06581, the entire disclosure of which is hereby incorporated by reference.

Some embodiments of the invention provide a unit dose of a therapeutic latanoprost solution comprising: about 1.5 µg of latanoprost per unit dose of solution; SAE-CD; pharmaceutically acceptable aqueous liquid carrier; and potassium sorbate of about 0.05 to about 0.2% by weight (or about 0.5% by wt.) of the unit dose, and wherein the solution is suitable for ophthalmic administration to a subject in need thereof.

Some embodiments of the invention also provide a method of treating preventing or ameliorating in a subject a latanoprost-responsive disease, condition, symptom or disorder, the method comprising metering into the eye of the subject a therapeutically effective amount of latanoprost that is about 6 µg or less per day, delivered as 1 or more unit doses, wherein each unit dose consists essentially of about 1.5 µg (or 1 to 2 µg) of latanoprost; SAE-CD; potassium sorbate of about 0.05 to about 0.2% by weight of the unit dose; and a pharmaceutically acceptable aqueous liquid carrier.

In some embodiments, the pH ranges from 6 to 7; the molar ratio SAE-CD to latanoprost ranges from 4:1 to 21:1; the concentration of latanoprost ranges from 25 to 150 µg/mL; and/or the concentration of SAE-CD ranges from 1 to 50 mg/mL.

In some embodiments, the composition further comprises one or more viscosity modifiers, one or more tonicity modifiers, one or more buffering agents, one or more preservatives, one or more buffers, or a combination thereof. In some embodiments, the composition excludes BAK (benzalkonium chloride) and/or excludes a preservative. In some embodiments, the composition excludes a viscosity modifier. In some embodiments, the composition is self-preserved. In some embodiments, the formulation is isotonic. In some embodiments, the composition further comprises a gelling agent, suspending agent, buffer, preservative or a combination thereof.

In some embodiments, the viscosity of the composition is in the range of 1-20,000 cps.

In some embodiments, the aqueous composition is a liquid, suspension, syrup, cream or gel. A suspension can comprise other materials suspended in the formulation; although, the latanoprost would be dissolved in the formulation.

In some embodiments, a dose of latanoprost comprises a therapeutically effective amount thereof in a volume of composition of 15 to 150 µL.

In some embodiments, SAE-CD comprises a compound, or mixture of compounds, of the Formula 1:

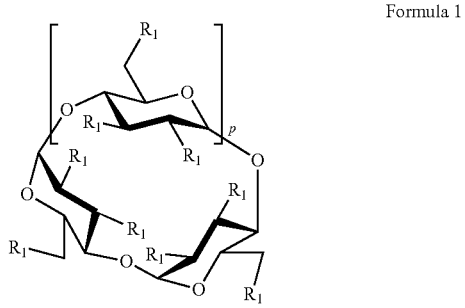

Formula 1 wherein:
p is 4, 5 or 6;
$R_1$ is independently selected at each occurrence from —OH or —SAET;
—SAE is a —O—($C_2$-$C_6$ alkylene)-$SO_3^-$ group, wherein at least one SAE is independently a —O—($C_2$-$C_6$ alkylene)-$SO_3^-$ group, a —O—$(CH_2)_g SO_3^-$ group, wherein g is 2 to 6, or 2 to 4, (e.g. —$OCH_2CH_2CH_2SO_3^-$ or —$OCH_2CH_2CH_2CH_2SO_3^-$); and
T is independently selected at each occurrence from the group consisting of pharmaceutically acceptable cations, which group includes, for example, $H^+$, alkali metals (e.g. $Li^+$, $Na^+$, $K^+$), alkaline earth metals (e.g., $Ca^{+2}$, $Mg^{+2}$), ammonium ions and amine cations such as the cations of ($C_1$-$C_6$)-alkylamines, piperidine, pyrazine, ($C_1$-$C_6$)-alkanolamine, ethylenediamine and ($C_4$-$C_8$)-cycloalkanolamine among others; provided that at least one $R_1$ is a hydroxyl moiety and at least one $R_1$ is —SAET.

In some embodiments, the SAE-CD is SAE-α-CD, SAE-β-CD or SAE-γ-CD. The SAE-CD can be SBE-CD, esp. SBE-β-CD. The average degree of substitution for the SAE-CD can range from 1 to 10, 2 to 8, 4 to 8, 6 to 7, or 5 to 7.

The invention includes all combinations of the embodiments and aspects disclosed herein. Accordingly, the invention includes the embodiments and aspects specifically disclosed, broadly disclosed, or narrowly disclosed herein, as well as combinations thereof and subcombinations of the individual elements of said embodiments and aspects.

These and other aspects of this invention will be apparent upon reference to the following detailed description, examples, claims, and attached figures.

BRIEF DESCRIPTION OF THE FIGURES

The following drawings are given by way of illustration only, and thus are not intended to limit the scope of the present invention.

DETAILED DESCRIPTION OF THE INVENTION

Figure 1:
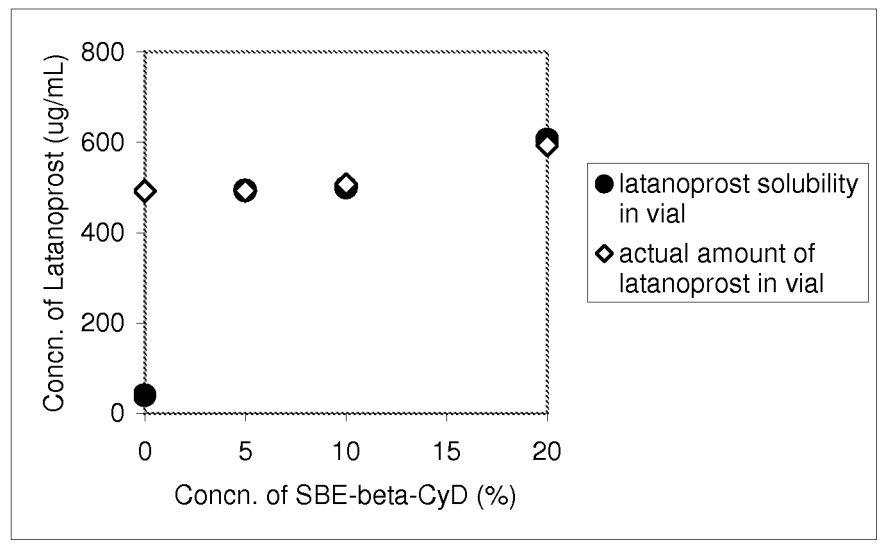
FIG. 1 depicts a phase solubility diagram for latanoprost in the presence of SBE-β-CD in an aqueous liquid carrier according to Example 5.

The present invention is directed to methods of treating ophthalmic diseases, symptoms, or disorders that are therapeutically responsive to latanoprost therapy by delivering aqueous compositions comprising latanoprost to ophthalmic tissues. The invention is also directed to methods, systems, devices, and compositions for delivering aqueous solution composition comprising latanoprost to ophthalmic tissues. The systems of the invention comprise an administration device, and a composition of the invention. The composition of the invention comprises latanoprost, an aqueous carrier and SAE-CD.

SAE-CD increases the shelf-life of an aqueous formulation comprising SAE-CD as compared to an aqueous formulation excluding SAE-CD. SAE-CD increases the stability of latanoprost against photolytic degradation (UV-B) and hydrolytic degradation. SAE-CD increases the aqueous solubility of latanoprost as compared to an aqueous formulation excluding SAE-CD.

The SAE-CD included in the composition of the invention is sulfoalkyl ether cyclodextrin (SAE-CD) derivative (e.g. CAPTISOL® and ADVASEP®), which is an anionic cyclodextrin derivative. The SAE-CD can be a compound or mixture of compounds of the Formula 1.

The terms "alkylene" and "alkyl," as used herein (e.g., in the —O—($C_2$-$C_6$-alkylene)$SO_3^-$ group or in the alkylamine cations), include linear, cyclic, and branched, saturated and unsaturated (i.e., containing one double bond) divalent alkylene groups and monovalent alkyl groups, respectively. The term "alkanol" in this text likewise includes both linear, cyclic and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl)cyclic alcohols.

When at least one $R_1$ in the CD molecule is —SAET, the degree of substitution, in terms of the —SAET moiety, is understood to be at least one. The term SAE is used to denote a sulfoalkyl (alkylsulfonic acid) ether moiety it being understood that the SAE moiety comprises a cation (T) unless otherwise specified. Accordingly, the terms SAE and SAET may, as appropriate, be used interchangeably herein.

Further exemplary SAE-CD derivatives include:

| SAEx-α-CD | SAEx-β-CD | SAEx-γ-CD |
|---|---|---|
| SEEx-α-CD | SEEy-β-CD | SEEz-γ-CD |
| SPEx-α-CD | SPEy-β-CD | SPEz-γ-CD |
| SBEx-α-CD | SBEy-β-CD | SBEz-γ-CD |
| SPtEx-α-CD | SPtEy-β-CD | SPtEz-γ-CD |
| SHEx-α-CD | SHEy-β-CD | SHEz-γ-CD | wherein SEE denotes sulfoethyl ether, SPE denotes sulfopropyl ether, SBE denotes sulfobutyl ether, SPtE denotes sulfopentyl ether, SHE denotes sulfohexyl ether, and the values "x", "y" and "z" represent the average degree of substitution as defined herein in terms of the number of sulfoalkyl ether groups per CD molecule. The salts thereof (with "T" as cation) are understood to be present.

Exemplary SAE-CD derivatives include SBE5.8-α-CD, SBE4-β-CD, SBE6-β-CD, SBE5-β-CD, SBE6.5-β-CD, SBE6.7-β-CD, SBE7-β-CD, SBE11-β-CD, SBE3.4-γ-CD, SBE4.2-γ-CD, SBE4.9-γ-CD, SBE5.2-γ-CD, SBE6.1-γ-CD, SBE7.5-γ-CD, SBE7.8-γ-CD and SBE5-γ-CD which correspond to SAE-CD derivatives herein.

The preparation of SAE-CD derivatives is disclosed in U.S. Pat. Nos. 5,376,645 and 5,134,127 to Stella et al. The SAE-CD derivatives or CD derivatives containing a sulfonate functional group can also be made according to Parmerter et al. (U.S. Pat. No. 3,426,011), Gadelle et al. (U.S. Pat. No. 5,578,719), Joullié et al. (U.S. Pat. Nos. 5,760,015 and 5,846,954), Buchanan et al. (U.S. Pat. Nos. 6,610,671 and 6,479,467), Perrier et al. (U.S. Pat. No. 6,524,595), Uchiyama et al. (U.S. Pat. No. 5,512,665), Lammers et al. (*Recl. Trav. Chim. Pays-Bas* (1972), 91(6), 733-742); *Staerke*(1971), 23(5), 167-171), Qu et al. (*J. Inclusion Phenom. Macro. Chem.*, (2002), 43, 213-221), Yoshinaga (Japanese Patent No. JP 05001102; U.S. Pat. No. 5,241,059), Zhang et al. (PCT International Publication No. WO 01/40316), Adam et al. (*J. Med. Chem.* (2002), 45, 1806-1816), and Tarver et al. (*Bioorganic & Medicinal Chemistry* (2002), 10, 1819-1827). SAE-CD can be purchased from CyDex Pharmaceuticals, Inc. (Lenexa, Kans.).

The various species of SAE-CD derivative can differ in their degree of substitution by functional groups, the number of carbons in the sulfoalkyl groups, their molecular weight, the number of glucopyranose units contained in the base cyclodextrin used to form the derivatized cyclodextrin and or their substitution patterns. In addition, the derivatization of a cyclodextrin with sulfoalkyl groups occurs in a controlled, although not exact manner. For this reason, the degree of substitution is actually a number representing the average number of functional groups per cyclodextrin (for example, SBE7-β-CD, has an average of 7 substitutions per cyclodextrin). Thus, it has an average degree of substitution (ADS) of about 7. In addition, the regiochemistry of substitution of the hydroxyl groups of the cyclodextrin is variable with regard to the substitution of specific hydroxyl groups of the hexose ring. For this reason, substitution of the different hydroxyl groups is likely to occur during manufacture of the derivatized cyclodextrin, and a particular derivatized cyclodextrin will possess a preferential, although not exclusive or specific, substitution pattern. Given the above, the molecular weight of a particular derivatized cyclodextrin composition may vary from batch to batch.

Within a given SAE-CD derivative composition, the substituents of the CD derivative(s) thereof can be the same. For example, SAE moieties can have the same type of alkylene (alkyl) radical upon each occurrence in a CD derivative composition. In such an embodiment, the alkylene radical in the SAE moiety might be ethyl, propyl, butyl, pentyl or hexyl in each occurrence in a CD derivative composition.

In a single parent CD molecule, there are 3v+6 hydroxyl moieties available for derivatization. Where v=4 (α-CD), "y" the degree of substitution for the moiety can range in value from 1 to 17. Where v=5 (β-CD), "y" the degree of substitution for the moiety can range in value from 1 to 20. Where v=6 (γ-CD), "y" the degree of substitution for the moiety can range in value from 1 to 23. In general, "y" also ranges in value from 1 to 3v+g, where g ranges in value from 0 to 5. "y" may also range from 1 to 2v+g, or from 1 to 1v+g.

The degree of substitution (DS) for a specific moiety (SAE, for example) is a measure of the number of SAE substituents attached to an individual CD molecule, in other words, the moles of substituent per mole of CD. Therefore, each substituent has its own DS for an individual CD derivative species. The average degree of substitution (ADS) for a substituent is a measure of the total number of substituents present per CD molecule for the distribution of CD derivatives within a CD derivative composition of the invention. Therefore, SAE4.0-CD has an ADS (per CD molecule) of 4.0.

A SAE-CD derivative composition of the invention comprises a distribution of different CD derivative species or molecules. More specifically, a SAE-CD derivative composition comprises plural SAE-CD species each having a specific individual degree of substitution with regard to the SAE substituent. As a consequence, the average DS (ADS) for SAE of a SAE-CD derivative composition represents an average of the individual DS (IDS) values of the population of individual molecules in the composition. For example, a SAE5.2-CD composition comprises a distribution of plural SAEx-CD molecules, wherein x (the DS for SAE groups) might range from 1 to 10-11 for individual CD molecules; however, the population of SAE-CD molecules is such that the average value for x (the ADS for SAE groups) is 5.2.

Some embodiments of the invention include a SAE-CD derivative wherein a minority of the sulfoalkyl substituent moieties is located at the C-6 position, and a majority of the sulfoalkyl substituent moieties is located at the C-2 and/or C-3 position. Another embodiment of the invention includes a SAE-CD derivative wherein a majority of the sulfoalkyl substituent moieties is located at the C-6 position, and a minority of the sulfoalkyl substituent moieties is located at the C-2 and/or C-3 position. Another embodiment of the invention includes a SAE-CD derivative wherein the sulfoalkyl substituent moieties are substantially evenly distributed among the C-2, C-3 and C-6 positions.

The amount and/or concentration of SAE-CD in the composition can be varied as needed or as described herein to provide a composition that possesses a desired physical property, provide therapeutic effectiveness in subjects to which the composition is administered, and/or achieve a desired performance in an administration device. SAE-CD can be present in an amount sufficient to solubilize and/or stabilize the latanoprost. The aqueous carrier can be present in an amount sufficient to aid in dissolution of the latanoprost and form a solution of sufficient volume and sufficiently low viscosity to permit administration with an administration device. In some embodiments, SAE-CD is present at a concentration of about 1 to 150 mg/mL, 1 to 100 mg/mL, 0.5 to 100 mg/mL, 1 to 50 mg/mL, 5 to 20 mg/mL, or about 10 to 50 mg/mL or about 1 mg/mL, about 5 mg/mL, about 10 mg/mL, about 15 mg/mL, about 20 mg/mL, about 50 mg/mL, about 100 mg/mL or about 150 mg/mL of composition. The SAE-CD can be present in an amount of 100 μg to 1000 mg per unit dose.

In some embodiments, the aqueous composition is viscous, mucoadhesive, or both viscous and mucoadhesive. The viscosity of the aqueous composition can be controlled by varying the concentration of SAE-CD. Higher concentrations of SAE-CD result in increased viscosity, and vice versa, as demonstrated in the table below for CAPTISOL® (SBE7-β-CD).

| SBE7-β-CD % w/w | Density (g/mL) | Viscosity (Cp, 25 C.) |
|---|---|---|
| 59.4 | 1.320 | 527.0 |
| 49.4 | 1.259 | 51.9 |
| 39.7 | 1.202 | 17.0 |
| 29.8 | 1.149 | 5.91 |
| 21.5 |  | 3.06 |
| 19.7 | 1.095 | 2.78 |
| 10.75 |  | 1.84 |
| 8.5 | 1.041 | 1.75 |
| 5.15 |  | 1.23 |
| 0.0 | 1.002 | 1 | slope = 0.0053
y-intercept = 0.995
correlation = 0.9989

The viscosity of the formulation will generally be less than 1000 cps or in the range of 1-20,000 cps for a liquid composition of the invention and will generally be less than 100 cps.

Viscosity of the composition can also be controlled by use of a viscosity modifier (viscosity modifying agent). As used herein, a "viscosity modifier" refers to an agent or combination of agents that can alter the viscosity of the aqueous composition of the invention. A viscosity modifier may be used to increase (viscosity enhancer) or decrease (viscosity-reducing agent) the viscosity of the aqueous composition. In general, any liquid suitable for ophthalmic administration can be used as a viscosity-reducing agent. Exemplary viscosity-reducing agents include water, aqueous buffer, organic solvent, surfactant, and combinations thereof. Suitable viscosity enhancers include hydrophilic polymers (water soluble polymers, water gellable polymers, and/or water swellable polymers) as described herein.

In some embodiments, the viscosity modifier is carboxymethylcellulose, which is a viscosity enhancer and promoter of mucoadhesion. The concentration of carboxymethylcellulose in the aqueous suspension or solution of the present invention can be about 0.1% to about 5%, or about 0.1% to about 2.5% by weight. In some embodiments, the carboxymethylcellulose is in the form of sodium carboxymethylcellulose substituted to a degree that the sodium content of the sodium carboxymethylcellulose is about 1% to about 20%.

Since the amount of SAE-CD in the composition can vary, the corresponding molar ratio of SAE-CD to latanoprost can vary. Increasing the molar ratio generally results in increased solubilization of latanoprost. The minimum molar ratio is generally about 2:1 or about 4:1. The maximum molar ratio is generally about 40:1 or less, or 30:1 or less or 21:1 or less. In some embodiments, the molar ratio ranges from 2:1 to 40:1, 2:1 to 30:1, 2:1 to 21:1, 4:1 to 40:1, 4:1 to 30:1 or 4:1 to 21:1.

SAE-CD increases the aqueous solubility of latanoprost. The phase solubility curve (FIG. 1) for latanoprost in the presence of SBE-β-CD (CAPTISOL®) was obtained according to Example 5. The intrinsic solubility of latanoprost in water, and in the absence of any solubilizing agent, is about 40 μg/mL. The invention provides a method of increasing the solubility of latanoprost in an aqueous composition, the method comprising including SAE-CD and latanoprost in the aqueous composition, wherein the molar ratio of SAE-CD to latanoprost, pH, concentration of SAE-CD, and concentration of latanoprost are as defined herein. In some embodiments, the SAE-CD increases the aqueous solubility of latanoprost by at least 10-fold.

Some embodiments of the invention include those wherein at least 50% wt., at least 75% wt., at least 90% wt., at least 95% wt., at least 98% wt., or all of the latanoprost is dissolved in the composition. As used in reference to the amount of dissolved latanoprost, a "substantial portion" is at least 20% wt., at least 30% wt., at least 40% wt., or at least 20% wt. and less than 50% wt. of the latanoprost.

The latanoprost can be present in the composition at a concentration of about 1 μg/mL to about 500 μg/mL, about 10 μg/mL to about 500 μg/mL, about 10 μg/mL to about 300 μg/mL, about 20 μg/mL to about 200 μg/mL, about 25 μg/mL to about 150 μg/mL, about 25 μg/mL to about 100 μg/mL, about 25 μg/mL to about 75 μg/mL, or about 50 to 150 μg/mL, or it can be present at a concentration of about 10 μg/mL, about 25 μg/mL, about 50 μg/mL, about 75 μg/mL, about 100 μg/mL, about 125 μg/mL, about 150 μg/mL, about 175 μg/mL, about 200 μg/mL, or about 300 μg/mL, depending on the volume to be administered.

By "complexed" is meant "being part of a clathrate or inclusion complex with", i.e., a complexed therapeutic agent is part of a clathrate or inclusion complex with a cyclodextrin derivative. By "major portion" is meant greater than about 50% by weight or greater than about 50% on a molar basis. Thus, a formulation according to the present invention may contain latanoprost wherein more than about 50% by weight is complexed with SAE-CD. The invention also includes embodiments wherein the latanoprost is not complexed with the SAE-CD or wherein a minor portion of the latanoprost is complexed with the SAE-CD derivative.

A liquid formulation of the invention may be converted to a solid formulation for reconstitution. A reconstitutable solid composition according to the invention comprises latanoprost, SAE-CD and optionally at least one other pharmaceutical excipient. This composition can be reconstituted with an aqueous liquid to form a liquid formulation according to the invention. The composition can comprise an admixture (minimal to no presence of an inclusion complex) of SAE-CD and latanoprost-containing solid and optionally at least one solid pharmaceutical excipient, such that a major portion of the latanoprost is not complexed with the SAE-CD prior to reconstitution. Alternatively, the composition can comprise a solid mixture of a SAE-CD and latanoprost, wherein a major portion of the latanoprost is complexed with the derivatized cyclodextrin prior to reconstitution. The reconstitutable solid can also comprise SAE-CD and latanoprost wherein substantially all or at least a major portion of the latanoprost is complexed with the derivatized cyclodextrin.

The reconstitutable formulation can be prepared according to any of the following processes. A liquid formulation of the invention is first prepared, then a solid is formed by lyophilization (freeze-drying), spray-drying, spray freeze-drying, antisolvent precipitation, various processes utilizing supercritical or near supercritical fluids, or other methods known to those of ordinary skill in the art to make a solid for reconstitution.

A liquid vehicle included in a formulation of the invention comprises an aqueous liquid carrier, such as water, aqueous alcohol, or aqueous organic solvent, or a non-aqueous liquid carrier.

Although not necessary, the formulation of the present invention may include one or more pharmaceutical excipients selected from the group consisting of a conventional preservative, antifoaming agent, antioxidant, buffering agent, acidifying agent, alkalizing agent, colorant, complexation-enhancing agent, cryoprotectant, electrolyte, gelling agent, glucose, emulsifying agent, oil, solubility-enhancing agent, stabilizer, tonicity modifier, flavors, sweeteners, complexing agents, fragrances, viscosity modifier, other excipients known by those of ordinary skill in the art for use in pharmaceutical formulations, and a combination thereof.

As used herein, the term "alkalizing agent" is intended to mean a compound used to provide alkaline medium for product stability. Suitable inorganic bases include ammonia, metal oxide and metal hydroxide. Suitable organic amine bases include primary amine, secondary amine, tertiary amine, imidazole, triazole, tetrazole, pyrazole, indole, diethanolamine, triethanolamine, diethylamine, methylamine, tromethamine (TRIS), aromatic amine, unsaturated amine, primary thiol, and secondary thiol. Specific exemplary compounds include ammonia solution, ammonium carbonate, diethanolamine, monoethanolamine, potassium hydroxide, sodium borate, sodium carbonate, sodium bicarbonate, sodium hydroxide, triethanolamine, diethanolamine, alkaline amino acids and trolamine and others known to those of ordinary skill in the art. A combination of bases can be used.

As used herein, the term "acidifying agent" is intended to mean a compound used to provide an acidic medium for product stability. Such compounds include, by way of example and without limitation, acetic acid, acidic amino acids, citric acid, fumaric acid and other alpha hydroxy acids, hydrochloric acid, ascorbic acid, phosphoric acid, sulfuric acid, tartaric acid and nitric acid and others known to those of ordinary skill in the art.

Inclusion of a conventional preservative in the ophthalmic solution formulation is optional, since the formulation is self-preserved by SAE-CD depending upon its concentration in solution. Nonetheless, a conventional preservative can be further included in the formulation if desired. Preservatives can be used to inhibit microbial growth in the compositions. The amount of preservative is generally that which is necessary to prevent microbial growth in the composition for a storage period of at least six months. As used herein, a conventional preservative is a compound used to at least reduce the rate at which bioburden increases, but maintains bioburden steady or reduces bioburden after contamination. Such compounds include, by way of example and without limitation, benzalkonium chloride, benzethonium chloride, benzoic acid, benzyl alcohol, cetyltrimethylammonium bromide, cetylpyridinium chloride, chlorobutanol, chlorocresol, chlorophenoxyethanol, disodium EDTA, imidazolidinyl urea, phenol, phenoxyethanol, phenylethyl alcohol, phenylmercuric nitrate, phenylmercuric acetate, phenylmercuric borate, phenoxypropanol, thimerosal, metacresol, myristylgamma picolinium chloride, potassium benzoate, potassium sorbate, sodium sorbate, sodium benzoate, sodium propionate, stabilized chlorine dioxide, sorbic acid, thymol, methylparaben, ethylparaben, propylparaben, butylparaben, salts of any of the above and others known to those of ordinary skill in the art. It is understood that some preservatives may interact with the CD derivative thus reducing the preservative effectiveness. Nevertheless, by adjusting the choice of preservative and the concentrations of preservative and the CD derivative adequately preserved formulations can be found.

As used herein, the term "antioxidant" is intended to mean an agent that inhibits oxidation and thus is used to prevent the deterioration of preparations by the oxidative process. Such compounds include, by way of example and without limitation, acetone, potassium metabisulfite, potassium sulfite, ascorbic acid, ascorbyl palmitate, citric acid, butylated hydroxyanisole, butylated hydroxytoluene, hypophosphorous acid, monothioglycerol, propyl gallate, sodium ascorbate, sodium citrate, sodium sulfide, sodium sulfite, sodium bisulfite, sodium formaldehyde sulfoxylate, thioglycolic acid, EDTA, pentetate, and sodium metabisulfite and others known to those of ordinary skill in the art.

As used herein, the term "buffering agent" is intended to mean a compound used to resist change in pH upon dilution or addition of acid or alkali. Such compounds include, by way of example and without limitation, acetic acid, sodium acetate, adipic acid, ammonium chloride, benzoic acid, sodium benzoate, boric acid, sodium bicarbonate, sodium borate, citric acid, glycine, maleic acid, monobasic sodium phosphate, dibasic sodium phosphate, HEPES, lactic acid, tartaric acid, potassium metaphosphate, potassium phosphate, monobasic sodium acetate, sodium bicarbonate, tris-hydroxymethylaminomethane, sodium tartrate, sodium citrate anhydrous and dehydrate, others known to those of ordinary skill in the art, salts of any of the above, and combinations thereof. Other buffers include citric acid/phosphate mixture, acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES (2-(N-morpholino)ethanesulfonic acid), BIS-TRIS (bis (2-hydroxyethyl)imino-tris(hydroxymethyl)methane), ADA (N-(2-acetamido)-2-iminodiacetic acid), ACES (N-(carbamoylmethyl)-2-aminoethanesulfonaic acid), PIPES (piperazine-N,N-bis(2-ethanesulfonic acid)), MOPSO (3-(N-morpholino)-2-hydroxypropanesulfonic acid), BIS-TRIS PROPANE (1,3-bis(tris(hydroxymethyl)methylamino)propane), BES (N,N-bis(2-hydroxyethyl)-2-aminoethanesulfonaic acid), MOPS (3-(N-morpholino)propanesulfonic acid), TES (N-tris(hydroxymethyl)methyl-2-aminoethanesulfonic acid), HEPES (N-(2-hydroxyethyl)piperazine-N'-(2-ethanesulfonic acid), DIPSO (3-(N,N-bis(2-hydroxyethyl)amino)-2-hydroxypropanesulfonic acid), MOBS (4-(N-morpholino)-butanesulfonic acid), TAPSO (3-(N-tris(hydroxymethyl)methylamino)-2-hydroxypropanesulfonic acid), TRIZMA™ (tris(hydroxymethylaminomethane), HEPPSO (N-(2-hydroxyethyl)piperazine-N'-(2-hydroxypropanesulfonic acid), POPSO (piperazine-N,N'-bis(2-hydroxypropanesulfonic acid)), TEA (triethanolamine), EPPS (N-(2-hydroxyethyl)piperazine-N'-(3-propanesulfonic acid), TRICINE (N-tris(hydroxymethyl)methylglycine), GLY-GLY (glycylglycine), BICINE (N,N-bis(2-hydroxyethyl)glycine), HEPBS (N-(2-hydroxyethyl)piperazine-N'-(4-butanesulfonic acid)), TAPS(N-tris(hydroxymethyl)methyl-3-aminopropanesulfonic acid), AMPD (2-amino-2-methyl-1,3-propanediol), and/or any other buffers known to those of skill in the art. Non-limiting exemplary combinations include citrate buffer with dextrose, citrate buffer with phosphate buffer.

The pH of the composition can range from about 5.5 to 7.5, about 5.5 to 7, or about 6 to 7, or the pH can be about 5.5, about 6, about 6.5, about 6.6, about 6.7, about 6.8, about 6.9, about 7 or about 7.5.

A complexation-enhancing agent can be added to a formulation of the invention. When such an agent is present, the ratio of cyclodextrin/active agent can be changed. A complexation-enhancing agent is a compound, or compounds, that enhance(s) the complexation of the active agent with the cyclodextrin. Suitable complexation enhancing agents include one or more pharmacologically inert water soluble polymers, hydroxy acids, and other organic compounds typically used in preserved formulations to enhance the complexation of a particular agent with cyclodextrins.

As used herein, the term "gelling agent" is an agent or combination of agents that cause in situ gellation of the aqueous composition. A gelling agent can be present in an amount (concentration) effective to promote gelling of the aqueous composition upon contact with the eye or with lacrimal fluid in the exterior of the eye. Suitable gelling agents include, by way of example and without limitation, thermosetting polymers such as tetra-substituted ethylene diamine block copolymers of ethylene oxide and propylene oxide (e.g., poloxamine 1307); polycarbophil; and polysaccharides such as gellan, carrageenan (e.g., kappa-carrageenan and iota-carrageenan), chitosan and alginate gums; and combinations thereof.

Hydrophilic polymers can be used as complexation-enhancing, solubility-enhancing, viscosity enhancer, and/or water activity reducing agents to improve the performance of formulations containing a cyclodextrin-based preservative. Loftsson has disclosed a number of polymers suitable for combined use with a cyclodextrin (underivatized or derivatized) to enhance the performance and/or properties of the cyclodextrin. Suitable polymers are disclosed in *Pharmazie* (2001), 56(9), 746-747; *International Journal of Pharmaceutics* (2001), 212(1), 29-40; Cyclodextrin: From Basic Research to Market, International Cyclodextrin Symposium, 10th, Ann Arbor, Mich., United States, May 21-24, 2000 (2000), 10-15 (Wacker Biochem Corp.: Adrian, Mich.); PCT International Publication No. WO 9942111; *Pharmazie*, 53(11), 733-740 (1998); *Pharm. Technol. Eur.*, 9(5), 26-34 (1997); *J. Pharm. Sci.* 85(10), 1017-1025 (1996); European Patent Application EP0579435; Proceedings of the International Symposium on Cyclodextrins, 9th, Santiago de Comostela, Spain, May 31-Jun. 3, 1998 (1999), 261-264 (Editor(s): Labandeira, J. J. Tones; Vila-Jato, J. L. Kluwer Academic Publishers, Dordrecht, Neth); *S.T.P. Pharma Sciences* (1999), 9(3), 237-242; ACS Symposium Series (1999), 737(Polysaccharide Applications), 24-45; *Pharmaceutical Research* (1998), 15(11), 1696-1701; *Drug Development and Industrial Pharmacy* (1998), 24(4), 365-370; *International Journal of Pharmaceutics* (1998), 163 (1-2), 115-121; Book of Abstracts, 216th ACS National Meeting, Boston, August 23-27 (1998), CELL-016, American Chemical Society; *Journal of Controlled Release*, (1997), 44/1 (95-99); *Pharm. Res.* (1997) 14(11), S203; *Investigative Ophthalmology & Visual Science*, (1996), 37(6), 1199-1203; Proceedings of the International Symposium on Controlled Release of Bioactive Materials (1996), 23rd, 453-454; *Drug Development and Industrial Pharmacy* (1996), 22(5), 401-405; Proceedings of the International Symposium on Cyclodextrins, 8th, Budapest, March 31-April 2, (1996), 373-376. (Editor(s): Szejtli, J.; Szente, L. Kluwer: Dordrecht, Neth.); *Pharmaceutical Sciences* (1996), 2(6), 277-279; *European Journal of Pharmaceutical Sciences*, (1996) 4(SUPPL.), S144; Third European Congress of Pharmaceutical Sciences Edinburgh, Scotland, UK Sep. 15-17, 1996; *Pharmazie*, (1996), 51(1), 39-42; *Eur. J. Pharm. Sci.* (1996), 4(Suppl.), S143; U.S. Pat. Nos. 5,472,954 and 5,324,718; *International Journal of Pharmaceutics* (Netherlands), (Dec. 29, 1995) 126, 73-78; Abstracts of Papers of the American Chemical Society, (2 Apr. 1995) 209(1), 33-CELL; *European Journal of Pharmaceutical Sciences*, (1994) 2, 297-301; *Pharmaceutical Research* (New York), (1994) 11(10), S225; *International Journal of Pharmaceutics* (Netherlands), (Apr. 11, 1994) 104, 181-184; and *International Journal of Pharmaceutics* (1994), 110(2), 169-77, the entire disclosures of which are hereby incorporated by reference.

Other suitable polymers are well-known excipients commonly used in the field of pharmaceutical formulations and are included in, for example, *Remington's Pharmaceutical Sciences, 18th Edition*, Alfonso R. Gennaro (editor), Mack Publishing Company, Easton, Pa., 1990, pp. 291-294; Alfred Martin, James Swarbrick and Arthur Commarata, *Physical Pharmacy. Physical Chemical Principles in Pharmaceutical Sciences, 3rd edition* (Lea & Febinger, Philadelphia, Pa., 1983, pp. 592-638); A. T. Florence and D. Altwood, (*Physicochemical Principles of Pharmacy, 2nd Edition*, MacMillan Press, London, 1988, pp. 281-334. The entire disclosures of the references cited herein are hereby incorporated by references. Still other suitable polymers include water-soluble natural polymers, water-soluble semi-synthetic polymers (such as the water-soluble derivatives of cellulose) and water-soluble synthetic polymers. The natural polymers include polysaccharides such as inulin, pectin, algin derivatives (e.g. sodium alginate) and agar, and polypeptides such as casein and gelatin. The semi-synthetic polymers include cellulose derivatives such as methylcellulose, hydroxyethylcellulose, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present invention.

The composition of the invention can be present in the form of a suspension, wherein the SAE-CD and latanoprost are dissolved in the aqueous liquid carrier and a particulate ion exchange resin is suspended in the liquid carrier. In some embodiments, the ion exchange resin is a cationic resin.

The cationic resin may provide an additional means of sustained release of the latanoprost. Such resins are characterized as either strongly acidic cation exchange resins, such as those having sulfonic acid functionality, or weakly acidic cation exchange resins, such as those having carboxylic acid functionality. The resin is incorporated as a finely divided powder, that is, 95% of the resulting particles (e.g. spheroidal particles) have a diameter less than 20.0 microns. The release of the latanoprost by the cation exchange resin and optional an anionic polymer is achieved when ions naturally present in the tear fluid, principally sodium and potassium, compete with the bound basic active for sites on the polymer vehicle and the ion exchange resin. Thus released, the basic active is presented to the eye surface for transport to the receptor sites.

Any pharmaceutical grade cationic ion exchange resin is suitable for the formulation and can be used either in the protonated (hydrogen) form or in the salt (e.g. sodium) form. Such resins are readily available, for example, from Rohm & Haas under the "Amberlite" tradename and from Dow Chemical Co. under the "Dowex" tradename.

The ion exchange resin component can be present in the composition at a level of from 0.05% to 10.0% by weight. The average particle size diameter of the resin ranges from 1 to 20 microns.

Typically, the average particle size of the commercially available form of the ion exchange material of choice is about 40 to 150 microns. Such particles can be conveniently reduced to a particle size in the range of about 1.0 to 25 microns by ball milling or according to other known techniques of particle size reduction.

As used herein, the term "stabilizer" is intended to mean a compound used to stabilize the therapeutic agent against physical, chemical, or biochemical process which would reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and other known to those of ordinary skill in the art.

One or more pharmaceutically acceptable salts or other solutes can be included in the composition in an amount required to bring tonicity of the composition into a physiologically acceptable range. As used herein, the term "tonicity modifier" is intended to mean a compound or compounds that can be used to adjust the tonicity of the liquid formulation. Exemplary tonicity modifiers include salts having sodium, potassium or ammonium cations and chloride, citrate, ascorbate, borate, phosphate, bicarbonate, sulfate, thiosulfate or bisulfite anions. As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those of ordinary skill in the art. Other tonicity modifiers include both inorganic and organic tonicity adjusting agents. Tonicity modifiers include, but are not limited to, ammonium carbonate, ammonium chloride, ammonium lactate, ammonium nitrate, ammonium phosphate, ammonium sulfate, ascorbic acid, bismuth sodium tartrate, boric acid, calcium chloride, calcium disodium edetate, calcium gluconate, calcium lactate, citric acid, dextrose, diethanolamine, dimethylsulfoxide, edetate disodium, edetate trisodium monohydrate, fluorescein sodium, fructose, galactose, glycerin, lactic acid, lactose, magnesium chloride, magnesium sulfate, mannitol, polyethylene glycol, potassium acetate, potassium chlorate, potassium chloride, potassium iodide, potassium nitrate, potassium phosphate, potassium sulfate, proplyene glycol, silver nitrate, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, triethanolamine, urea, urethan, uridine and zinc sulfate. In some embodiments, the tonicity of the liquid formulation approximates the tonicity of the tissues of the eye.

An osmotic agent can be used in the compositions to enhance the overall comfort to the patient upon delivery of the prostaglandin composition. Osmotic agents can be added to adjust the tonicity of SAE-CD containing solutions. Osmolality is related to concentration of SAE-CD in water. At SBE7-β-CD concentrations below about 11-13% w/v, the solutions are hypotonic or hypoosmotic with respect to blood and at SBE7-β-CD concentrations above about 11-13% w/v the SBE7-β-CD containing solutions are hypertonic or hyperosmotic with respect to blood. Suitable osmotic agents include any low molecular weight water-soluble species pharmaceutically approved for ophthalmic delivery such as sodium chloride. The formulation of the invention can also include biological salt(s), potassium chloride, or other electrolyte(s). A tonicity modifier can be an osmotic agent.

As used herein, the term "antifoaming agent" is intended to mean a compound or compounds that prevents or reduces the amount of foaming that forms on the surface of the liquid formulation. Suitable antifoaming agents include dimethicone, simethicone, octoxynol and others known to those of ordinary skill in the art.

As used herein, the term "bulking agent" is intended to mean a compound used to add bulk to the solid product and/or assist in the control of the properties of the formulation during lyophilization. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

As used herein, the term "cryoprotectant" is intended to mean a compound used to protect an active therapeutic agent from physical or chemical degradation during lyophilization. Such compounds include, by way of example and without limitation, dimethyl sulfoxide, glycerol, trehalose, propylene glycol, polyethylene glycol, and others known to those of ordinary skill in the art.

A solubility-enhancing agent can be added to the composition of the invention. A solubility-enhancing agent is a compound, or compounds, that enhance(s) the solubility of the latanoprost when in a liquid formulation. When such an agent is present, the ratio of cyclodextrin/latanoprost can be changed. Suitable solubility enhancing agents include one or more cyclodextrins, cyclodextrin derivatives, SAE-CD, organic solvents, detergents, soaps, surfactant and other organic compounds typically used in parenteral formulations to enhance the solubility of a particular agent. Exemplary solubility enhancers are disclosed in U.S. Pat. No.

6,451,339; however, other surfactants used in the pharmaceutical industry can be used in the formulation of the invention. Some suitable cyclodextrin include underivatized cyclodextrins and cyclodextrin derivatives, such as SAE-CD, SAE-CD derivatives, hydroxyalkyl ether cyclodextrin and derivatives, alkyl ether cyclodextrin and derivatives, sulfated cyclodextrin and derivatives, hydroxypropyl-β-cyclodextrin, 2-HP-β-CD, methyl-β-cyclodextrin, carboxyalkyl thioether derivatives, succinyl cyclodextrin and derivatives, and other cyclodextrin suitable for pharmaceutical use. SAE-CD cyclodextrins are particularly advantageous.

Suitable organic solvents that can be used include, for example, ethanol, glycerin, poly(ethylene glycol), propylene glycol, poloxamer, aqueous forms thereof and others known to those of ordinary skill in the art.

It should be understood, that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

A composition according to the invention can have its oxygen removed. For example, the headspace of the container with the liquid formulation is made oxygen free, substantially oxygen free, or oxygen-reduced by purging the headspace with an inert gas, such as nitrogen or argon, or by bubbling the inert gas through the liquid formulation. In this way, a substantial portion of the oxygen dissolved in, and/or in surface contact with the solution is removed. For long-term storage, the liquid formulation containing an active agent subject to oxidative degradation can be stored in an oxygen-free or oxygen-reduced environment. Removal of oxygen from the formulation will enhance preservation of the formulation against aerobic microbes; whereas, addition of oxygen to the formulation will enhance preservation against anaerobic microbes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "patient" or "subject" are taken to mean warm blooded animals such as mammals, for example, cats, dogs, mice, guinea pigs, horses, bovine cows, sheep, non-humans, and humans.

A composition of the invention will comprise an active agent present in an effective amount. By the term "effective amount", is meant the amount or quantity of active agent that is sufficient to elicit the required or desired response, or in other words, the amount that is sufficient to elicit an appreciable biological response when administered to a subject.

A liquid composition of the invention can be prepared as follows. A first method comprises the steps of: forming a first aqueous solution comprising a cyclodextrin derivative; forming a second solution or suspension comprising active agent; and mixing the first and second solutions to form the liquid formulation. A second method is similar to the first step except that the active agent is added directly to the first solution without formation of the second solution. A third method is similar to the first except that the cyclodextrin derivative is added directly to the second solution/suspension without formation of the first solution. A fourth method comprises the steps of: adding a solution/suspension comprising active agent to a powdered or particulate cyclodextrin derivative. A fifth method comprises the steps of: adding the active agent directly to the powdered or particulate cyclodextrin derivative; and adding a second solution. A sixth method comprises the steps of: creating the liquid formulation by any of the above methods and then isolating a solid material by lyophilization, spray-drying, spray-freeze-drying, antisolvent precipitation, a process utilizing a supercritical or near supercritical fluid, or other methods known to those of ordinary skill in the art to make a powder for reconstitution.

A composition of the invention can be sterilized by: 1) filtration through a filtration medium having a pore size of 0.1 microns or larger; 2) irradiation; and/or 3) autoclaving.

A dose of an ophthalmic formulation comprising the aqueous composition of the invention can be administered to the eye of a subject in need thereof.

The volume or amount of composition administered can vary according to the intended delivery target and administration device used. The amount of latanoprost in a dose or unit dose can vary according to the intended delivery target and administration device used.

The compositions can be administered via an administration device suitable for ophthalmic administration of pharmaceutical compositions. As used herein, an administration device is any pharmaceutically acceptable device adapted to deliver a composition of the invention to a subject's eye(s). An ophthalmic administration device can be a dropper, pipette, drop dispensing package, tube, eye spray device, eye wash unit, and other devices known to those of ordinary skill in the art.

An administration device can comprise a reservoir containing the aqueous composition of the invention. The amount of aqueous composition may vary according to the reservoir capacity. An administration device can comprise one or more unit doses. In general, the total volume of aqueous composition in an administration device comprises at least the volume of a single unit dose up to the volume of generally 60 to 240 unit doses. A device that comprises more than one unit dose is referred to as a multi-dose device. The volume of aqueous composition in a multi-dose device typically ranges from 100 µl to 10 mL, 200 µl to 5 ml, or 300 µl to 2.5 mL.

The fill volume for the reservoir of a multi-dose administration device must be sufficient to provide for the number of actuations required to provide the desired number of doses in a consistent manor. The reservoir of an administration device can comprise an overfill. As used herein, "overfill" is the amount or percentage of extra composition (either in terms of the volume or weight of the composition or the amount of drug in the composition) added to the composition in the reservoir to compensate for the tail-off characteristics of the device. In some embodiments, the overfill is at least about 1%, at least about 2.5%, at least about 5%, at least about 7.5%, at least about 10%, at least about 15%, at least about 25%, at least about 35%, at least about 45%, at least about 50% of the target volume or weight of composition in a unit dose or dose of the composition.

Packaging and containers suitable for use as multi-dose devices include, by way of example and without limitation, a bottle, vial, pipette, ampoule, syringe, blister, capsule or other devices. The packaging can be in a preservative free system such as blow/fill/seal dropper container or form/fill/seal dropper container.

The administration device can employ single use (single dose) or multi-use (multi-dose) packaging. An administration device can be used repeatedly with single use or multi-use packages and/or containers.

As used herein, a dose includes a unit dose, dose to subject, dose to eye, or other such term of art. Unless otherwise specified, the term a "unit dose" is a single dose, such as a single drop from an administration device. An administration of an effective amount, effective dose, or therapeutically effective amount to a subject can comprise one or more unit doses. In certain embodiments, the effective dose can be a single unit dose administered to one eye. In certain embodiments, the therapeutically effective amount can be two unit doses administered to one eye. In certain embodiments, the effective dose can be two unit doses, with one unit dose administered to each eye. In some embodiments, the therapeutically effective amount can be more than two unit doses, with more than one dose administered to an eye. The term "effective amount" or "effective dose" or "therapeutically effective amount" is the amount or quantity of active agent that is sufficient to elicit the required or desired therapeutic effect, or the amount that is sufficient to elicit an appreciable biological response when administered to a subject when given at one event or period of administration. A single period of administration can comprise administration of 1, 2 or more unit doses. For administration with a metered administration device, i.e., a device that provides a fixed volume or amount of composition upon actuation, e.g., pump, squeeze bottle, dropper, and other similar devices, the event of administration, for delivery of an effective dose, is a predetermined number of actuations of the device which releases a corresponding predetermined number of unit doses, e.g., 1 to 4 actuations of the administration device releases 1 to 4 unit doses in one or both eyes of a subject. The unit dose of latanoprost delivered is assumed to be the amount of latanoprost emitted from the administration device, i.e., the emitted dose.

The daily dose of latanoprost is generally about 0.75 µg to about 6 µg, about 0.75 µg to about 4.5 µg, about 0.75 µg to about 3 µg, or about 0.75 µg, or about 1.5 µg, depending on the disease, disorder, condition or symptom being treated, in accordance with the 2007 *Physician's Desk Reference* (*PDR*). The dose required to achieve a desired clinical endpoint, clinical benefit or therapeutic benefit can be lower than the corresponding dose indicated in the PDR.

An appropriate dosage, frequency and duration of administration, i.e., treatment regimen, to be used in any particular situation will be readily determined by one of skill in the art without undue experimentation, and will depend, among other factors, on the particular disease, disorder, symptom or condition to be treated or prevented, on the age, weight and general physical condition of the subject, and on other medication being administered to the subject. Response to treatment according to the present method be monitored and the treatment regimen be adjusted if necessary in light of such monitoring.

The ophthalmic composition of the invention can be prescribed and administered to a subject as needed to provide the desired level of clinical benefit. A desired dosage of latanoprost can be metered by administration of a known number of drops into the eye. For example, for a drop volume of 25 µL, administration of 1-6 drops will deliver 25-150 µL of the composition. In general, a subject can be administered 1 to 4 drops per eye at a dosing frequency of 1 to 4 times per day. In some embodiments, a subject is administered 1 to 2 drops per eye at a dosing frequency of 1 to 2 times per day, or 1 drop per eye per day of an aqueous composition as described herein. It should be noted that the typical volume of a drop from an eye dropper ranges from about 15 to about 100 µL, about 20 to about 80 µL, about 25 to about 50 µL, or about 30 to about 40 µL.

The composition can be administered at any time of day or night. In some embodiments, the composition is administered to a subject in the evening or within an hour prior to the time the subject goes to sleep. In some embodiments, the composition is administered in the daytime and/or the nighttime.

A dose of latanoprost can also be administered once daily, every other day, once every two days, seven days per week, once every week, once every month, for an extended period of time, such as several days, weeks, or even longer, or even less frequently.

Some embodiments of the invention include those wherein a unit dose of aqueous composition comprises about 1 to about 2 µg or about 1.5 µg in a volume of composition of about 25 to about 50 µL or about 30 to about 40 µL, wherein the unit dose is administered to a subject in need thereof once or twice daily per eye.

In terms of the phrase "per eye", it should be understood that an eye suffering from a latanoprost-responsive disease, disorder, condition or symptom is being referred to. Accordingly, a composition of the invention can be administered to one or both eyes of subject in need thereof, since one or both eyes, respectively, might be in need of treatment.

The composition of the invention can be administered to a subject in need thereof for the treatment of one or more disorders, diseases, conditions, or symptoms that are therapeutically responsive to latanoprost, e.g. one or more latanoprost-responsive disorders, diseases, conditions, or symptoms. A latanoprost-responsive disease, condition, symptom or disorder is one wherein a subject suffering from such will receive a clinical benefit after administration of a latanoprost-containing composition according to the invention. Exemplary disorders, diseases or symptoms include glaucoma, open-angle glaucoma, elevated intraocular pressure, and ocular hypertension.

Figure 2:
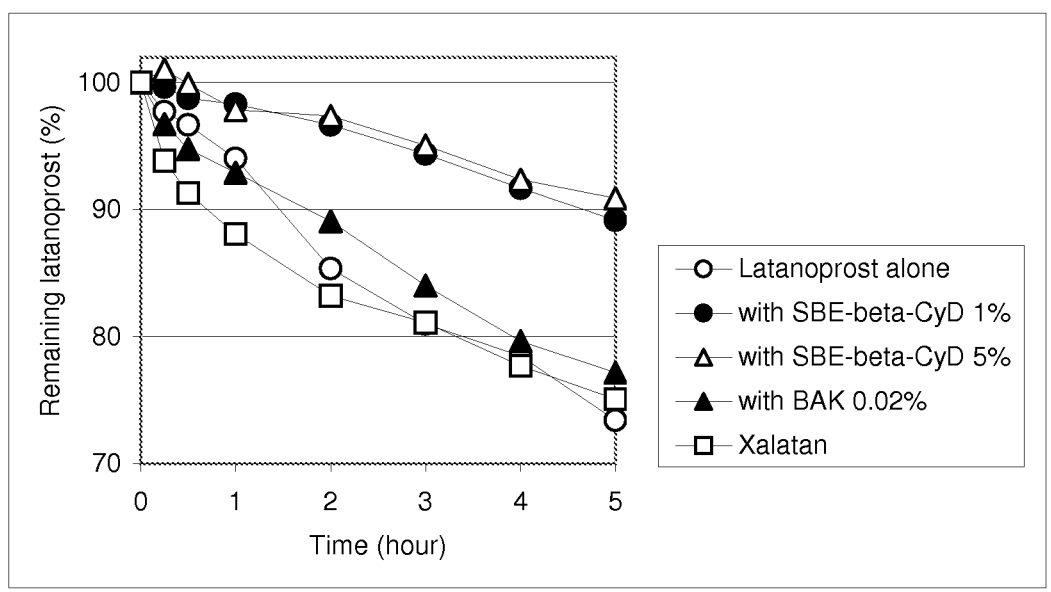
FIG. 2 depicts a plot of percentage of latanoprost remaining in solution versus storage time for aqueous composition containing latanoprost and exposed to UV-B radiation according to Example 6.

A composition of the invention possesses enhanced stability of latanoprost against UV-B catalyzed photolytic degradation thereof as compared to the commercial XALATAN® formulation or as compared to an aqueous liquid formulation excluding SAE-CD. FIG. 2 depicts a plot of data obtained from a study of the stability of latanoprost (concentration of latanoprost remaining versus period of storage) conducted according to Example 6. The invention provides a method of increasing the stability of latanoprost in an aqueous composition against photolytic degradation catalyzed by UV-B radiation, the method comprising including SAE-CD in the composition in an amount sufficient to suppress or reduce the rate or extent of photolytic degradation of latanoprost when exposed to UV-B radiation as compared to the rate or extent of photolytic degradation observed in an otherwise similar aqueous composition excluding SAE-CD and exposed to the same conditions.

Figure 3:
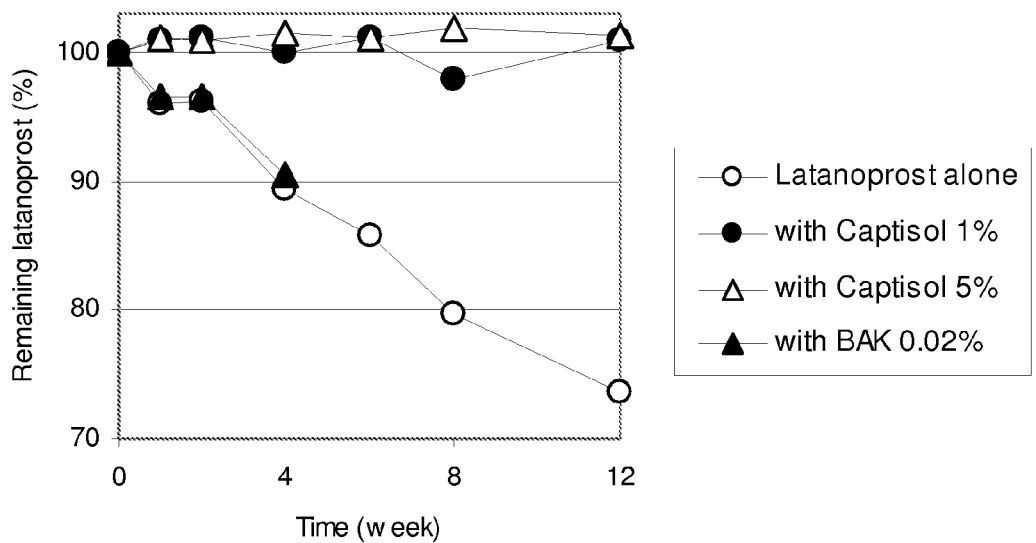
FIGS. 3-5 depict plots of percentage of latanoprost remaining in solution versus storage time for aqueous composition containing latanoprost and varying in pH and concentration of SBE-β-CD according to Example 7.
Figure 4:
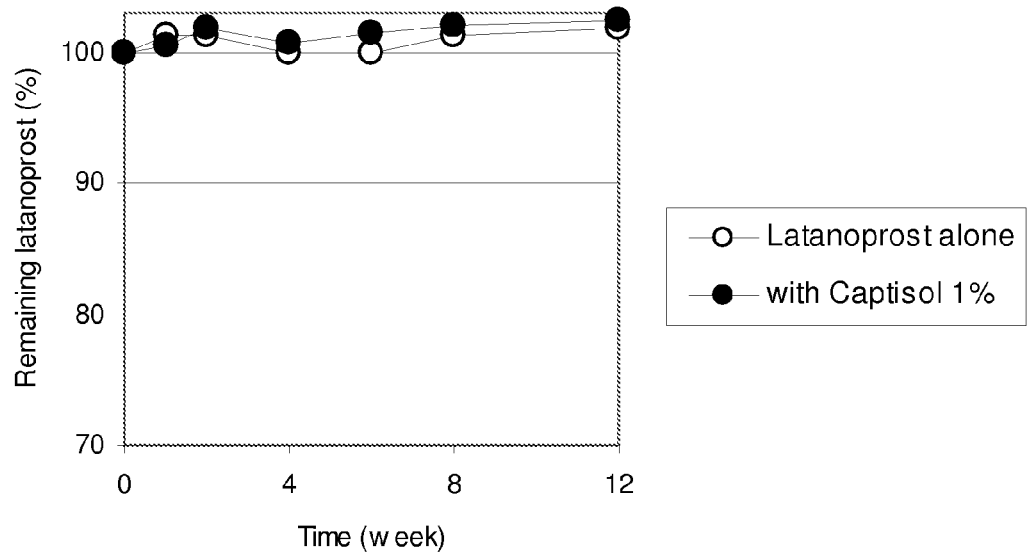
Figure 5:
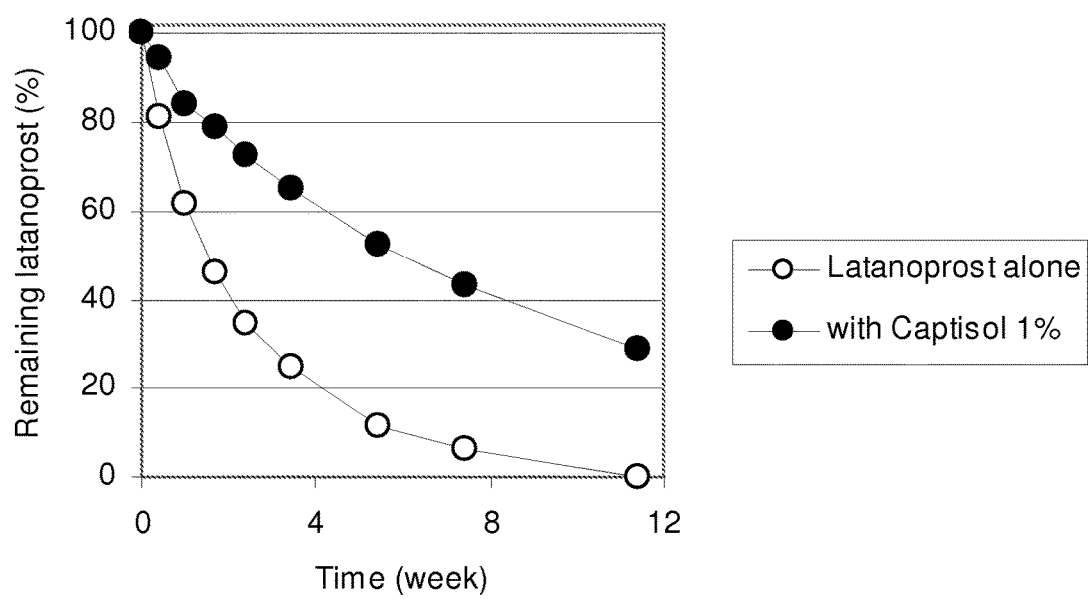

The composition also possesses enhanced stability against hydrolytic degradation of latanoprost in aqueous solution as compared to the commercial XALATAN® formulation or as compared to an aqueous liquid formulation excluding SAE-CD. FIGS. 2-4 depict plot of data obtained from studies (Example 7) of the stability of latanoprost to solutions of different pH. The invention provides a method of increasing the stability of latanoprost in an aqueous composition against hydrolytic degradation, the method comprising including SAE-CD in the composition in an amount sufficient to suppress or reduce the rate or extent of hydrolytic degradation of latanoprost as compared to the rate or extent of hydrolytic degradation observed in an otherwise similar aqueous composition excluding SAE-CD and exposed to the same conditions.

The compositions of the invention can generally have a storage shelf life of at least 3 mo at 60° C., or at least one year at room temp or at least two years at room temperature. In this case, shelf life is determined only as regards the increase in the amount of latanoprost degradation by-products or a reduction in the amount of latanoprost remaining in the composition. For example, for a composition having a shelf life of at least six months, the composition will not demonstrate an unacceptable and substantial increase in the amount of degradants during the storage period of at least six months. The criteria for acceptable shelf-life are set as needed according to a given product and its storage stability requirements. In other words, the amount of degradants in a composition having an acceptable shelf-life will not increase beyond a predetermined value during the intended period of storage. On the other hand, the amount of degradants of a composition having an unacceptable shelf-life will increase beyond the predetermined value during the intended period of storage.

In view of the above description and the examples below, one of ordinary skill in the art will be able to practice the invention as claimed without undue experimentation. The foregoing will be better understood with reference to the following examples that detail certain procedures for the preparation of molecules, compositions and formulations according to the present invention. All references made to these examples are for the purposes of illustration. The following examples should not be considered exhaustive, but merely illustrative of only a few of the many embodiments contemplated by the present invention.

Example 1

Preparation of an Aqueous Liquid Composition of SAE-CD and Latanoprost

SAE-CD is added to an aqueous liquid carrier to form a solution of SAE-CD. Latanoprost is added to the solution of SAE-CD with mixing to form the aqueous liquid composition of the invention. Excipients are optionally included in the formulation. The pH of the composition is in the range of 6 to 7. The molar ratio of SAE-CD to latanoprost is in the range of 2:1 to 40:1 or 4:1 to 21:1. The concentration of latanoprost in the final composition is in the range of 10 to 300 μg/mL, 25 to 150 μg/mL, 25 to 100 μg/mL, 25 to 75 μg/mL, or 50 to 150 μg/mL, or about 10 μg/mL, about 25 μg/mL, about 50 μg/mL, about 75 μg/mL, about 100 μg/mL, about 150 μg/mL or about 300 μg/mL. The concentration of SAE-CD is in the range of 0.5 to 100 mg/mL, 1 to 50 mg/mL, 5 to 20 mg/mL, or about 10 to 50 mg/mL of about 1 mg/mL, about 5 mg/mL, about 10 mg/mL, about 15 mg/mL, or about 20 mg/mL.

Example 2

Preparation of an Aqueous Liquid Composition of SBE-β-CD and Latanoprost

Preservative-free aqueous liquid compositions can be made according to Example 1 or as follows.

A buffered isotonic solution is prepared at pH 6.7 using 50 mM phosphate buffer solution (sodium dihydrogen phosphate monohydrate, disodium hydrogen phosphate anhydrous and sodium chloride) containing 10 mg/mL SBE-β-CD. To 100 ml of this solution is added 5 mg latanoprost with stirring until the latanoprost is completely dissolved. The resulting solution contains approximately 0.05 mg/mL latanoprost. The solution is filtered and sterilized using 0.2 μm PVDF filter, and 0.4 ml of filtered solution is filled into each of sterile single-use eye-dropper containers, such as form-fill-seal LDPE.

| Ingredient | Comp. 2a | Comp. 2b | Comp. 2c | Comp. 2d |
|---|---|---|---|---|
| SBE7-β-CD (mg/mL) | 10 (1% w/v) | 5 (0.5% w/v) | 1 (0.1% w/) | 15 (1.5% w/v) |
| Latanoprost (μg/mL | 50 (0.005% w/v) | 100 (0.01% w/v) | 50 (0.005% w/v) | 150 (0.015% w/v) |
| Molar Ratio (SAE-CD to Latanoprost) | 40:1 | 10:1 | 4:1 | 20:1 |
| Water (mL) | 100 | 100 | 100 | 100 |
| Buffer (mM) | 50 ($NaH_2PO_4$ + $Na_2HPO_4$) | 10 (Citric Acid + Sodium Citrate) | 50 ($NaH_2PO_4$ + $Na_2HPO_4$) | None - adjust with NaOH and HCl |
| pH | 6.7 | 6 | 7 | 5.5 |

Example 3

Preparation of an Aqueous Liquid Composition of SBE-γ-CD and Latanoprost

Viscosity-enhanced aqueous liquid compositions can be made according to Example 1 or as follows.

A buffered isotonic solution is prepared at pH 6.7 using 50 mM phosphate buffer solution (sodium dihydrogen phosphate monohydrate, disodium hydrogen phosphate anhydrous and sodium chloride) containing 10 mg/mL SBE-gamma-CD and 17% poloxamer 407 (a polyoxyethylene-polyoxypropylene-polyoxyethylene block copolymer, supplied as Pluronic™ F-127 of BASF). To 100 ml of this solution is added 5 mg latanoprost with stirring until the latanoprost is completely dissolved. The resulting solution contains approximately 0.05 mg/mL latanoprost. The solution is filtered and sterilized using 0.2 μm PVDF filter, and 2.5 ml of filtered solution is filled into each of 5 mL clear low density polyethylene bottle with a clear low density polyethylene dropper tip, a high density polyethylene screw cap and a tamper-evident overcap.

| Ingredient | Comp. 3a | Comp. 3b | Comp. 3c | Comp. 3d |
|---|---|---|---|---|
| SBE4.2-γ-CD (mg/mL) | 5 (0.5% w/v) | 5 (0.5% w/v) | 1 (0.1% w/) | 15 (1.5% w/v) |
| Latanoprost (μg/mL | 50 (0.005% w/v) | 100 (0.01% w/v) | 50 (0.005% w/v) | 150 (0.015% w/v) |
| Molar Ratio (SAE-CD to Latanoprost) | 22:1 | 11:1 | 4:1 | 22:1 |
| Viscosity modifier (% w/v) | Poloxamer-407 17% | Polypropylene glycol 15% | Glycerin 3% | Polyethylene glycol 10% |
| Water (mL) | 100 | 100 | 100 | 100 |
| Buffer (mM) | 50 ($NaH_2PO_4$ + $Na_2HPO_4$) | 50 ($NaH_2PO_4$ + $Na_2HPO_4$) | 50 ($NaH_2PO_4$ + $Na_2HPO_4$) | 50 ($NaH_2PO_4$ + $Na_2HPO_4$) |
| pH | 6.7 | 6.7 | 6.7 | 6.7 |

Example 4

Preparation of an Aqueous Liquid Ophthalmic Composition of SBE-β-CD and Latanoprost Aqueous liquid compositions with added preservative can be made according to Example 1 or as follows.

A buffered isotonic solution is prepared at pH 6.7 using 50 mM phosphate buffer solution (sodium dihydrogen phosphate monohydrate, disodium hydrogen phosphate anhydrous and sodium chloride) containing 10 mg/mL SBE-beta-CD and potassium sorbate 0.2%. To 100 ml of this solution is added 5 mg latanoprost with stirring until the latanoprost is completely dissolved. The resulting solution contains approximately 0.05 mg/mL latanoprost. The solution is filtered and sterilized using 0.2 μm PVDF filter, and 2.5 ml of filtered solution is filled into each of 5 mL clear low density polyethylene bottle with a clear low density polyethylene dropper tip, a high density polyethylene screw cap and a tamper-evident overcap.

| Ingredient | Comp. 4a | Comp. 4b | Comp. 4c | Comp. 4d |
|---|---|---|---|---|
| SBE7-β-CD (mg/mL) | 10 (1% w/v) | 5 (0.5% w/v) | 1 (0.1% w/) | 15 (1.5% w/v) |
| Latanoprost (μg/mL) | 50 (0.005% w/v) | 100 (0.01% w/v) | 50 (0.005% w/v) | 150 (0.015% w/v) |
| Preservative (mg/mL) | Potassium sorbate 2 (0.2% w/v) | Methyl-paraben 0.05% | Sorbic acid 0.2% | Phenyl-mercuric nitrite 0.002% |
| Molar Ratio (SAE-CD to Latanoprost) | 40:1 | 10:1 | 4:1 | 20:1 |
| Water (mL) | 100 | 100 | 100 | 100 |
| Buffer (mM) | 50 ($NaH_2PO_4$ + $Na_2HPO_4$) | 50 ($NaH_2PO_4$ + $Na_2HPO_4$) | 50 ($Na_2HPO_4$) ($NaH_2PO_4$ + $Na_2HPO_4$) | 50 ($NaH_2PO_4$ + $Na_2HPO_4$) |
| pH | 6.7 | 6.7 | 6.7 | 6.7 |

Example 5

Determination of Phase Solubility Curve of Latanoprost in the Presence of SAE-CD Aqueous compositions containing latanoprost and different amounts of SBE-β-CD were prepared. Latanoprost (1 mg was measured into aluminum weighing boats (size 4×12×4 mm) by using a microbalance. The boats were put into the amber glass vials (Kimble vial, 1 dram) with Teflon-lined screw caps. Using a Rainin pipetman, 2.0 mL of SBE-β-CD test solution (0, 5, 10, or 20% w/v) were added to each vial. Each vial was capped, vortexed, placed on a rocker platform and gently mixed at room temperature. After 24 hours, the test vials were removed from the rocker platform, the solutions were centrifuged at 2500 rpm for 5 min, and the supernatants were filtered through 0.22 micron Millipore PVDF Millex-GV filters and the pH measured. The latanoprost in the aliquots was assayed by HPLC.

|  | Latanoprost (mg/mL) | pH |
|---|---|---|
| without CAPTISOL ® | 40.0 | 8.57 |
| with 5% w/v CAPTISOL ® | >500 | 7.41 |
| with 10% w/v CAPTISOL ® | >500 | 6.93 |

In solutions containing at least 5% w/v of SAE-CD, the solubility of latanoprost exceeded 500 μg/mL.

Example 6

Determination of Photolytic Stability of Aqueous Compositions of Latanoprost Latanoprost was measured in weighing boats (size 4×12×4 mm) by using a microbalance. The boats were put into 50 mL volumetric flask and 100 mM isotonic phosphate buffer (pH 6.7) was added to the flask. The flask was shaken, sonicated and vortexed over an hour. The solution was filtered through a PVDF filter with 20 mL of plastic syringe. SBE-β-CD 0, 1, 5% w/v and BAK 0.02% w/v were measured into each 10 mL volumetric flask and the filtered latanoprost solution were added to them. The flasks were shaken for a few minutes at R.T, and then these solutions and XALATAN® were put into quartz vessels. The Rayonet photochemical chamber reactor was used for the irradiation with RMR-3000A lamp. At various time points, the latanoprost in the aliquots was assayed by HPLC, and the solution pH's were measured before and after the light irradiation.

SAE-CD concentrations of 1% or 5% w/v were sufficient to suppress photolytic degradation of latanoprost as compared to a solution excluding SAE-CD.

Latanoprost HPLC Conditions:

| Instrument: | Perkin-Elmer Series 200 Autosampler, Pump, and Diode Array Detector |
|---|---|
| Column: | Supelco Discovery RP Amide C16 4.6 × 250 mm 5 μm |
| Mobile Phase: | Phosphate acid aqueous pH 3:Acetonitrile (50:50) |
| Wavelength | λ = 214 nm |
| Flow Rate: | 1.0 mL/min |
| Injection Volume | 20 μL |

Example 7

Determination of Hydrolytic Stability of Aqueous Compositions of Latanoprost Latanoprost was measured in weighting boats (size 4×12×4 mm) by using a microbalance. The boats were put into 50 mL volumetric flask and 10 mM or 100 mM isotonic phosphate buffer (pH 5.5, 6.7 and 8.0) was added to the flask. The flask was shaken, sonicated and vortexed over an hour. The solution was filtered through a PVDF filter with 20 mL of plastic syringe. SBE-β-CyD 0, 1, 2.5, 5% w/v or BAK 0.02% were measured into 6-dram amber vials, and the filtered latanoprost solution (12 mL) was added to each vials. The vials were shaken for a few minutes at R.T, and then there were kept at 60° C. At various time points, the latanoprost in the aliquots was assayed by HPLC and the solution pH's were measured.

SAE-CD concentrations of 1% or 5% w/v were sufficient to suppress hydrolytic degradation of latanoprost at pH 5.5 and 6.7 (60° C.) as compared to a solution excluding SAE-CD. SAE-CD was also able to substantially reduce hydrolytic degradation of latanoprost at pH 8 (60° C.) as compared to a solution excluding SAE-CD.

Example 8

Measuring Viscosity of Aqueous Solutions Containing SAE-CD Using a Cone and Plate Viscometer A Brookfield Programmable DV-III+ Rheometer, CPE-40 cone and CPE 40Y plate (Brookfield Engineering Laboratories, Middleboro, Mass.) is used to make measurements on 0.5 ml samples at 1, 2, 3, 5 and 10 rpm. Samples are sheered for approximately 5 revolutions prior to each measurement. This allows for accurate rheological characterization of the samples. The temperature of all samples is equilibrated to 25+/−1 degree centigrade using a double wall viscometer cone supplied with water from an electronically controlled thermostatic circulating water bath (Model, 8001, Fisher Scientific, Pittsburgh, Pa.). The viscometer is calibrated using 5 and 50 centipoise using silicon oil calibration standards. Viscosity measurements are made at 5 or more rotation speeds to look for sheer thinning behavior (viscosities that decrease as the rate of sheer increases). Higher rotation speeds result in increased rates of sheer.

Example 9

Preparation of a Stabilized Aqueous Liquid Ophthalmic Composition of SBE-β-CD and Latanoprost Aqueous liquid compositions with added stabilizer can be made according to Example 1 or as follows.

A buffered isotonic solution is prepared at pH 6.7 using 50 mM phosphate buffer solution (sodium dihydrogen phosphate monohydrate, disodium hydrogen phosphate anhydrous and sodium chloride) containing 10 mg/mL SBE-beta-CD and disodium EDTA dehydrate 0.04%. To 100 ml of this solution is added 5 mg latanoprost with stirring until the latanoprost is completely dissolved. The resulting solution contains approximately 0.05 mg/mL latanoprost. The solution is filtered and sterilized using 0.2 μm PVDF filter, and 2.5 ml of filtered solution is filled into each of 5 mL clear low density polyethylene bottle with a clear low density polyethylene dropper tip, a high density polyethylene screw cap and a tamper-evident overcap.

| Ingredient | Comp. 11a | Comp. 11b | Comp. 11c |
|---|---|---|---|
| SBE7-β-CD (mg/mL) | 10 (1% w/v) | 10 (1% w/v) | 10 (1% w/v) |
| Latanoprost (μg/mL) | 50 (0.005% w/v) | 50 (0.005% w/v) | 50 (0.005% w/v) |
| Stabilizer (mg/mL) | Na$_2$-EDTA dehydrate (0.04% w/v) | Sodium bisulfate 0.1% | Sodium sulfate 0.2% |
| Molar Ratio (SAE-CD to LATAN) | 40:1 | 40:1 | 40:1 |
| Water (mL) | 100 | 100 | 100 |
| Buffer (mM) | 50 (NaH$_2$PO$_4$ + Na$_2$HPO$_4$) | 50 (NaH$_2$PO$_4$ + Na$_2$HPO$_4$) | 50 (NaH$_2$PO$_4$ + Na$_2$HPO$_4$) |
| pH | 6.7 | 6.7 | 6.7 |

Example 10

Preparation of an Aqueous Liquid Ophthalmic Composition of SBE-β-CD and Latanoprost Aqueous liquid compositions with added gelling agent and stabilizer can be made according to Example 1 or as follows.

A buffered isotonic solution is prepared at pH 6.7 using 50 mM phosphate buffer solution (sodium dihydrogen phosphate monohydrate, disodium hydrogen phosphate anhydrous and sodium chloride) containing 10 mg/mL SBE-beta-CD and disodium EDTA dehydrate 0.04%, iota-carrageenan 0.5%, iota-carrageenan with calcium 0.3% and glycerin 1.5%. To 100 ml of this solution is added 5 mg latanoprost with stirring until the latanoprost is completely dissolved. The resulting solution contains approximately 0.05 mg/mL latanoprost. The solution is filtered using 0.2 μm PVDF filter, and 2.5 ml of filtered solution is filled into each of 5 mL clear low density polyethylene bottle with a clear low density polyethylene dropper tip, a high density polyethylene screw cap and a tamper-evident overcap.

| Ingredient | Comp. 12 |
|---|---|
| SBE7-β-CD (mg/mL) | 10 (1% w/v) |
| Latanoprost (μg/mL) | 50 (0.005% w/v) |
| Stabilizer (% w/v) | Na$_2$-EDTA dehydrate 0.04% |
| Gelling agent (mg/mL) | Iota-carrageenan (0.5% w/v) |
| Gelling agent (mg/mL) | Iota-carrageena + Calcium (0.3%) |
| Viscosity modifier (% w/v) | glycerin (1.5% w/v) |
| Molar Ratio (SAE-CD to LATAN) | 40:1 |
| Water (mL) | 100 |
| Buffer (mM) | 50 (NaH$_2$PO$_4$ + Na$_2$HPO$_4$) |
| pH | 6.7 |

Example 11

Preparation of a Preserved Aqueous Suspension Ophthalmic Composition of SBE-β-CD and Latanoprost Aqueous suspension compositions with added preservative can be made according to Example 1 or as follows.

Finely divided Amberlite IRP-69 resin, a sodium poly (styrene-divinyl benzene) sulfonate, and latanoprost are mixed in 50% of the total water volume component to form a uniform dispersion. The Carbopol-934P (suspending agent) is added slowly as an aqueous dispersion. The mixture is homogenized at high speed. The other ingredients, 10 mg/mL SBE-beta-CD and potassium sorbate (preservative) are added as aqueous solutions. The final volume is made on addition of water. The resultant products are white uniform suspensions.

Example 12

Preparation of an In Situ Gelling Preserved Aqueous Ophthalmic Composition of SBE-β-CD and Latanoprost An in situ-gelling aqueous suspension compositions with added preservative can be made according to Example 1 or as follows.

Gelrite is a purified anionic heteropolysaccharide derived from gellan gum. Latanoprost is dissolved in water containing 10 mg/mL SBE-beta-CD, 1% Gelrite gellan gum (gelling agent) and 0.2% potassium sorbate (preservative).

The entire disclosures of the references cited herein are hereby incorporated in their entirety. The term about is taken to mean+/− 10% of a corresponding or indicated value.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. An aqueous composition comprising: an aqueous carrier; SAE-β-CD; and latanoprost, wherein the pH of the composition ranges from 6.6 to 7; the molar ratio of SAE-β-CD to latanoprost ranges from 2:1 to 40:1; the concentration of latanoprost ranges from 10 to 500 μg/mL; and the concentration of SAE-β-CD ranges from 1 to 100 mg/mL, with the proviso that the composition does not comprise hyaluronate.

2. A unit dose of an aqueous composition comprising:
an aqueous carrier;
SAE-β-CD;
latanoprost; and
potassium sorbate, wherein the pH of the composition ranges from 6.6 to 7; the molar ratio of SAE-β-CD to latanoprost ranges from 2:1 to 40:1; the concentration of latanoprost is about 50 μg/mL; the concentration of SAE-β-CD ranges from 1 to 100 mg/mL and the concentration of the potassium sorbate is about 0.05 to about 0.2% by weight of the unit dose, and wherein the solution is suitable for ophthalmic administration to a subject in need thereof, with the proviso that the composition does not comprise hyaluronate.

3. A system for treating a disease, disorder, condition or symptom of the eye in a subject in need thereof, the system comprising:
the aqueous composition of claim 1; and
an administration device for ophthalmic administration of the aqueous composition to the subject, wherein the composition is provided in the device.

4. The system according to claim 3, wherein the administration device is a dropper, drop-dispensing package, tube, eye spray device, or eye wash unit.

5. The system according to claim 3, wherein the administration device comprises plural unit doses of latanoprost.

6. The aqueous composition of any of claims 1-5, wherein at least 98% wt. of the latanoprost is dissolved in the composition.

7. An aqueous composition comprising:
an aqueous carrier;
SAE-β-CD,
latanoprost; and
one or more agents selected from one or more viscosity modifiers, one or more tonicity modifiers, one or more buffering agents, one or more preservatives, one or more buffers, one or more suspending agents, one or more gelling agents, or a combination thereof;
wherein the pH of the composition ranges from 6.6 to 7, the molar ratio of SAE-β-CD to latanoprost ranges from 2:1 to 40:1, the concentration of latanoprost ranges from 10 to 500 μg/mL, and the concentration of SAE-β-CD ranges from 1 to 100 mg/mL, with the proviso that the composition does not comprise hyaluronate.

8. The aqueous composition of claim 7, wherein the viscosity of the composition is in the range of 1-20,000 cps.

9. The aqueous composition of any one of claim 1 or 3-5, wherein: the molar ratio of SAE-β-CD to latanoprost ranges from 4:1 to 21:1; the concentration of latanoprost ranges from 25 to 150 μg/mL; and/or the concentration of SAE-β-CD ranges from 1 to 50 mg/mL.

10. The aqueous composition any one of claims 1-5, wherein the composition is a liquid, syrup, cream or gel.

11. The aqueous composition of any one of claims 1-5, wherein a dose of latanoprost comprises a therapeutically effective amount thereof in a volume of composition of 15 to 150 μL.

12. The aqueous composition of any one of claims 1-5, wherein SAE-β-CD comprises a compound, or mixture of compounds, of the Formula 1:

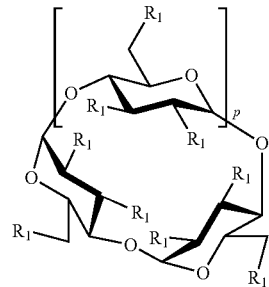

Formula 1 wherein:
p is 5;
$R_1$ is independently selected at each occurrence from —OH or —SAET; —SAE is a —O—($C_2$-$C_6$ alkylene)-$SO_3^-$ group, wherein at least one SAE is independently a —O—($C_2$-$C_6$ alkylene)-$SO_3^-$ group, a —O—$(CH_2)_g$ $SO^-$ group, wherein g is 2 to 6; and
T is independently selected at each occurrence from the group consisting of pharmaceutically acceptable cations, provided that at least one $R_1$ is a hydroxyl moiety and at least one $R_1$ is —SAET.

13. The aqueous composition of claim 12, wherein average degree of substitution for the SAE-β-CD ranges from 5 to 7.

14. The aqueous composition of claim 7, wherein the viscosity of the composition is less than 1000 cps.

15. The aqueous composition of claim 12, wherein g is 2 to 4.

16. The aqueous composition of claim 1, wherein the aqueous carrier is selected from water, aqueous alcohol, aqueous organic solvent, or any combinations thereof.

17. The aqueous composition of claim 2, wherein the aqueous carrier is selected from water, aqueous alcohol, aqueous organic solvent, or any combinations thereof.

18. The aqueous composition of claim 7, wherein the aqueous carrier is selected from water, aqueous alcohol, aqueous organic solvent, or any combinations thereof.

19. An aqueous composition consisting essentially of: an aqueous carrier; SAE-β-CD; and latanoprost, wherein the pH of the composition ranges from 6.6 to 7; the molar ratio of SAE-β-CD to latanoprost ranges from 2:1 to 40:1; the concentration of latanoprost ranges from 10 to 500 μg/mL; and the concentration of SAE-β-CD ranges from 1 to 100 mg/mL, wherein the composition excludes a preservative, and the composition is self-preserved.

* * * * *

UNITED STATES PATENT AND TRADEMARK OFFICE
CERTIFICATE OF CORRECTION

PATENT NO. : 10,463,677 B2
APPLICATION NO. : 13/128319
DATED : November 5, 2019
INVENTOR(S) : Naomi Esaki et al.

It is certified that error appears in the above-identified patent and that said Letters Patent is hereby corrected as shown below:

On the Title Page

On Page 2, Column 2, Item (56), Line 52, under Other Publications, delete "Comostela" and insert --Compostela--.

On Page 2, Column 2, Item (56), Line 59, under Other Publications, delete "sulfobytul" and insert --sulfobutyl--.

In the Specification

In Column 5, Line 60, delete "Staerke(1971)" and insert --Staerke (1971)--.

In Column 5, Line 60, delete "167-171)" and insert --167-171--.

In Column 6, Lines 5-6, delete "and or" and insert --and/or--.

In Column 10, Lines 55-56, delete "McIlvaine" and insert --Mcilvaine--.

In Column 10, Line 57, delete "Stanhagen" and insert --Stenhagen--.

In Column 10, Line 61, delete "aminoethanesulfonaic" and insert --aminoethanesulfonic--.

In Column 10, Line 62, delete "N,N-" and insert --N,N'- --.

In Column 11, Line 35, delete "gellation" and insert --gelation--.

In Column 11, Line 65, delete "Comostela" and insert --Compostela--.

In Column 12, Lines 42-43, delete "(Physicochemical" and insert --Physicochemical--.

Signed and Sealed this
Second Day of June, 2020

Andrei Iancu
*Director of the United States Patent and Trademark Office*

CERTIFICATE OF CORRECTION (continued)
U.S. Pat. No. 10,463,677 B2

In Column 13, Line 43, delete "acetyltryptophonate" and insert --acetyltryptophanate--.

In Column 14, Line 8, delete "proplyene" and insert --propylene--.

In Column 14, Line 54, delete "dimethyl sulfoxide" and insert --dimethylsulfoxide--.

In Column 19, Line 2, delete "mo" and insert --months--.

In Column 20, Line 11 (Approx.), delete "(µg/mL" and insert --(µg/mL)--.

In Column 20, Line 54 (Approx.), delete "(µg/mL" and insert --(µg/mL)--.

In Column 21, Line 27 (Approx.), delete "(µg/mL" and insert --(µg/mL)--.

In Column 21, Line 47 (Approx.), delete "(1" and insert --1--.

In Column 23, Line 2, delete "sheered" and insert --sheared--.

In Column 23, Line 12 (Approx.), delete "sheer" and insert --shear--.

In Column 23, Line 13 (Approx.), delete "sheer" and insert --shear--.

In Column 23, Line 14 (Approx.), delete "sheer" and insert --shear.--.

In Column 23, Line 43 (Approx.), delete "(µg/mL" and insert --(µg/mL)--.

In Column 24, Line 17 (Approx.), delete "(µg/mL" and insert --(µg/mL)--.

In Column 24, Line 21 (Approx.), delete "carrageena" and insert --carrageenan--.

In the Claims

In Column 26, Line 6, Claim 10, delete "composition any" and insert --composition of any--.